US009605078B2

(12) United States Patent
Bertozzi et al.

(10) Patent No.: US 9,605,078 B2
(45) Date of Patent: Mar. 28, 2017

(54) PICTET-SPENGLER LIGATION FOR PROTEIN CHEMICAL MODIFICATION

(71) Applicant: THE REGENTS OF THE UNIVERSITY OF CALIFORNIA, Oakland, CA (US)

(72) Inventors: Carolyn Bertozzi, Berkeley, CA (US); Paresh Agarwal, Berkeley, CA (US); Ellen M. Sletten, Somerville, MA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/443,149

(22) PCT Filed: Nov. 15, 2013

(86) PCT No.: PCT/US2013/070421
§ 371 (c)(1),
(2) Date: May 15, 2015

(87) PCT Pub. No.: WO2014/078733
PCT Pub. Date: May 22, 2014

(65) Prior Publication Data
US 2015/0291699 A1    Oct. 15, 2015

Related U.S. Application Data

(60) Provisional application No. 61/727,501, filed on Nov. 16, 2012.

(51) Int. Cl.
| | | |
|---|---|---|
| C07D 209/12 | (2006.01) | |
| C07K 16/32 | (2006.01) | |
| C07D 311/92 | (2006.01) | |
| C07D 405/12 | (2006.01) | |
| C07D 495/04 | (2006.01) | |
| C07D 498/04 | (2006.01) | |

(52) U.S. Cl.
CPC ............ *C07K 16/32* (2013.01); *C07D 209/12* (2013.01); *C07D 311/92* (2013.01); *C07D 405/12* (2013.01); *C07D 495/04* (2013.01); *C07D 498/04* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,816,567 A | 3/1989 | Cabilly et al. |
| 4,935,496 A | 6/1990 | Kudo et al. |
| 5,075,046 A | 12/1991 | Stoll |
| 5,089,261 A | 2/1992 | Nitecki et al. |
| 5,100,992 A | 3/1992 | Cohn et al. |
| 5,134,192 A | 7/1992 | Feigen et al. |
| 5,166,309 A | 11/1992 | Maj et al. |
| 5,171,264 A | 12/1992 | Merril |
| 5,213,891 A | 5/1993 | Maj et al. |
| 5,219,564 A | 6/1993 | Zalipsky et al. |
| 5,225,539 A | 7/1993 | Winter |
| 5,275,838 A | 1/1994 | Merrill |
| 5,281,698 A | 1/1994 | Nitecki |
| 5,298,643 A | 3/1994 | Greenwald |

(Continued)

FOREIGN PATENT DOCUMENTS

| | | |
|---|---|---|
| EP | 0239400 | 9/1987 |
| EP | 0519596 | 12/1992 |

(Continued)

OTHER PUBLICATIONS

Van Maarseveen, Jan H. et al, "An approach to canthine derivatives using the intramolecular pictet-spengler condensation." Tetrahedron (1995) 51(16) p. 4841-4852.*
Agarwal, Paresh and Bertozzi, Carolyn, "Modification of the pictet-spengler reaction for protein conjugation." Abstracts of papers, 244th ACS national meeting and exposition (presented Aug. 21, 2012) ORGN-487.*
Van Maarseveen, Jan H. et al, "An approach to canthine derivatives using the intramolecular pictet-spengler condensation." Tetrahedron (1995) 51(6) p. 4841-4852.*
Agarwal, et al., Bioconjgate Chem., 24:846-851 (2013).
Alam et al., J. Am. Chem. Soc., 132:9546-9548 (2010).
Alam et al., Chem. Commun., 47: 9066-9068 (2011).
Carrico et al., Nature, Chemical Biology, 3(6): 321-322 (2007).
Chen et al., Nature Methods, 2(2): 99-104 (2005).
Cho et al., PNAS, 108(22):9060-9065 (2011).
Dirksen et al., Oxime Ligation, Angew. Chem. Int. Ed., 45:7581-7584 (2006).
Ducry and Stump, Bioconjugate Chem., 21:5-13 (2010).

(Continued)

*Primary Examiner* — Fred Reynolds
(74) *Attorney, Agent, or Firm* — Morgan, Lewis & Bockius LLP; Jeffry S. Mann; Todd Esker

(57) ABSTRACT

Aldehyde- and ketone-functionalized proteins are promising new substrates for the development of chemically modified biotherapeutics and protein-based materials. Their reactive carbonyl groups are typically conjugated with a-effect nucleophiles, such as substituted hydrazines and alkoxyamines, to generate hydrazones and oximes, respectively. However, the resulting C=N linkages are susceptible to hydrolysis under physiologically relevant conditions, which limits their utility in biological systems. Here we introduce a Pictet-Spengler ligation that is based on the classic Pictet-Spengler reaction of aldehydes and tryptamine nucleophiles. The ligation exploits the bioorthogonal reaction of aldehydes and alkoxyamines to form an intermediate oxyiminium ion; this intermediate undergoes intramolecular C—C bond formation with an indole nucleophile to form an oxacarboline product that is hydrolytically stable. The reaction was utilized for site-specific chemical modification of glyoxal- and formylglycine-functionalized proteins, including an aldehyde-tagged variant of the therapeutic monoclonal antibody Herceptin. In conjunction with techniques for site-specific introduction of aldehydes into proteins, the Pictet-Spengler ligation offers a new means to generate stable bioconjugates for medical and materials applications.

14 Claims, 12 Drawing Sheets

(56) References Cited

U.S. PATENT DOCUMENTS

| | | | |
|---|---|---|---|
| 5,312,808 A | 5/1994 | Shorr et al. | |
| 5,321,095 A | 6/1994 | Greenwald | |
| 5,324,844 A | 6/1994 | Zalipsky | |
| 5,349,001 A | 9/1994 | Greenwald | |
| 5,352,756 A | 10/1994 | Meldal | |
| 5,405,877 A | 4/1995 | Greenwald et al. | |
| 5,446,090 A | 8/1995 | Harris | |
| 5,455,027 A | 10/1995 | Zalipsky et al. | |
| 5,470,829 A | 11/1995 | Prisell et al. | |
| 5,478,805 A | 12/1995 | Shorr et al. | |
| 5,502,167 A | 3/1996 | Waldmann et al. | |
| 5,530,101 A | 6/1996 | Queen et al. | |
| 5,558,864 A | 9/1996 | Bendig et al. | |
| 5,565,332 A | 10/1996 | Hoogenboom et al. | |
| 5,567,422 A | 10/1996 | Greenwald | |
| 5,585,089 A | 12/1996 | Queen et al. | |
| 5,605,976 A | 2/1997 | Martinez et al. | |
| 5,612,368 A * | 3/1997 | Andrieux | C07C 259/06 514/190 |
| 5,612,460 A | 3/1997 | Zalipsky | |
| 5,614,549 A | 3/1997 | Greenwald et al. | |
| 5,618,528 A | 4/1997 | Coper et al. | |
| 5,637,749 A | 6/1997 | Greenwald | |
| 5,643,575 A | 7/1997 | Martinez et al. | |
| 5,650,388 A | 7/1997 | Shorr et al. | |
| 5,672,662 A | 9/1997 | Harris et al. | |
| 5,681,567 A | 10/1997 | Martinez et al. | |
| 5,686,110 A | 11/1997 | Greenwald et al. | |
| 5,693,493 A | 12/1997 | Robinson et al. | |
| 5,698,417 A | 12/1997 | Robinson et al. | |
| 5,705,154 A | 1/1998 | Dalie et al. | |
| 5,730,990 A | 3/1998 | Greenwald et al. | |
| 5,739,208 A | 4/1998 | Harris | |
| 5,750,078 A | 5/1998 | Shitara et al. | |
| 5,756,593 A | 5/1998 | Martinez et al. | |
| 5,770,403 A | 6/1998 | Dalie et al. | |
| 5,808,096 A | 9/1998 | Zalipsky | |
| 5,824,778 A | 10/1998 | Ishikawa et al. | |
| 5,824,784 A | 10/1998 | Kinstler et al. | |
| 5,840,900 A | 11/1998 | Greenwald et al. | |
| 5,874,500 A | 2/1999 | Rhee et al. | |
| 5,880,131 A | 3/1999 | Greenwald et al. | |
| 5,900,461 A | 5/1999 | Harris | |
| 5,902,588 A | 5/1999 | Greenwald et al. | |
| 5,919,442 A | 7/1999 | Yin et al. | |
| 5,919,455 A | 7/1999 | Greenwald et al. | |
| 5,932,462 A | 8/1999 | Harris et al. | |
| 5,965,119 A | 10/1999 | Greenwald et al. | |
| 5,965,566 A | 10/1999 | Greenwald et al. | |
| 5,985,263 A | 11/1999 | Lee et al. | |
| 5,990,237 A | 11/1999 | Bentley et al. | |
| 6,011,042 A | 1/2000 | Greenwald et al. | |
| 6,013,283 A | 1/2000 | Greenwald et al. | |
| 6,077,939 A | 6/2000 | Wei et al. | |
| 6,113,906 A | 9/2000 | Greenwald et al. | |
| 6,127,355 A | 10/2000 | Greenwald et al. | |
| 6,177,087 B1 | 1/2001 | Greenwald et al. | |
| 6,180,095 B1 | 1/2001 | Greenwald et al. | |
| 6,194,580 B1 | 2/2001 | Greenwald et al. | |
| 6,214,966 B1 | 4/2001 | Harris | |
| 2004/0086979 A1 | 5/2004 | Zhang et al. | |
| 2005/0033031 A1 | 2/2005 | Couto | |
| 2007/0135485 A1 | 6/2007 | Gillig et al. | |

FOREIGN PATENT DOCUMENTS

| | | |
|---|---|---|
| EP | 0592106 | 4/1994 |
| WO | WO 9013540 | 11/1990 |
| WO | WO 91/09967 | 7/1991 |
| WO | WO 9109967 | 7/1991 |
| WO | WO 9200748 | 1/1992 |
| WO | WO 9216555 | 10/1992 |
| WO | WO 9404193 | 3/1994 |
| WO | WO 9414758 | 7/1994 |
| WO | WO 9417039 | 8/1994 |
| WO | WO 9418247 | 8/1994 |
| WO | WO 9428937 | 12/1994 |
| WO | WO 9511924 | 5/1995 |
| WO | WO 9513312 | 5/1995 |
| WO | WO 9600080 | 1/1996 |
| WO | WO 9621469 | 7/1996 |
| WO | WO 9623794 | 8/1996 |
| WO | WO 9703106 | 1/1997 |
| WO | WO 9807713 | 2/1998 |
| WO | WO 9841562 | 9/1998 |
| WO | WO 9845331 | 10/1998 |
| WO | WO 9845332 | 10/1998 |
| WO | WO 9848837 | 11/1998 |
| WO | WO 9930727 | 6/1999 |
| WO | WO 9932134 | 7/1999 |
| WO | WO 9933483 | 7/1999 |
| WO | WO 9945964 | 9/1999 |
| WO | WO 9953951 | 10/1999 |
| WO | WO 0126692 | 4/2001 |
| WO | WO 2008008398 | 1/2008 |
| WO | WO 2009/150865 | 12/2009 |
| WO | WO 2014/078566 | 5/2014 |

OTHER PUBLICATIONS

Esser-Kahn and Francis, Protein-Polymer Hybrids, Angew. Chem. INt. Ed. 47:3751-3754 (2008).
Geoghegan and Stroh, Bioconjugate Chem., 3:138-146 (1992).
Gilmore et al., Bioorganic Chemistry, Agnew. Chem. Int. Ed., 45:5307-5311 (2006).
Glazer, Annu. Rev. Biochem. 39(1): 101-130 (1970).
Hang and Bertozzi, J. Am. Chem. Soc., 123:1242-1243 (2001).
Hermkens et al., Tetrahedron, 46(3):833-846 (1990).
Hutchins et al., Chem. Biol., 18(3):299-303 (2011).
Hudak et al., Protein Chemistry, Agnew. Chem. Int. Ed., 51:4161-4165 (2012).
Hudak et al., J. Am. Chem. Soc., 133:16127-16135 (2011).
Ishikawa et al., J. Am. Chem. Soc., 123:7734-7735 (2001).
Jameson and Ross, Chem. Rev., 110(5):2685-2708 (2010).
Jencks, Progress in Physical Organic Chemistry, Cohen, Streitwieser, Jr., Taft, Eds., vol. 2, 63-128 (1964).
Kalia and Raines, Agnew. Chem. Int. Ed. Engl., 47(39): 7523-7526 (2008).
Kim et al., J. Am. Chem. Soc., 134(24):9918-9921 (2012).
Kirkup et al., Tetrahedron Letters, 30(49):6809-6812 (1989).
Krop et al., Journal of Clinical Oncology, 30(26):3234-3241 (2012).
Lee et al., Org. Lett. 13(20): 5564-5567 (2011).
Mahal et al., Science, 276:1125-1128 (1997).
Maresh et al., J. Am. Chem. Soc., 130(2): 710-723 (2008).
Michalet et al., Chem. Rev., 106(5): 1785-1813 (2006).
Molina et al., Tetrahedron, 52(16):5833-5844 (1996).
Mueller et al., Bioconjugate Chem., 1:325-330 (1990).
Nakagawa et al., J. Chem. Soc. Chem. Commun., 7:463-464 (1988).
Nystrom, The EMBO Journal, 24:1311-1317 (2005).
O'Shannessy et al., Analytical Biochemistry, 163:204-209 (1987).
Padlan, Molecular Immunology, 38(4/5):489-498 (1991).
Plate et al., J. Org. Chem., 52:555-560 (1987).
Rabuka et al., Nat. Protoc., 7(6): 1052-1067 (2012).
Rashidian et al., J. Am. Chem. Soc., 134(20):8455-8467 (2012).
Riechmann, et al., Nature, 332:323-327 (1988).
Roguska et al., PNAS USA, 91:969-973 (1994).
Sadamoto et al., J. Am. Chem. Soc., 126:3755-3761 (2004).
Sasaki et al., Bioorganic & Medicinal Chemistry Letters, 18:4550-4553 (2008).
Scheck et al., J. Am. Chem. Soc., 130:11762-11770 (2008).
Shen et al., Letters, Nature Biotechnology, 30(2): 184-191 (2012).
Shi et al., Nat. Methods, 9(5):499-503 (2012).
Sletten and Bertozzi, Agnew. Chem. Int. Ed. Engl., 48(38): 6974-6998 (2009).
Smith et al., PNAS USA, 88: 10540-10543 (1991).
Stephanopoulos and Francis, Nature, Chemical Biology, 7:876-884 (2011).
Studnicka et al., Protein Engineering, 7(6):805-814 (1994).
Tai et al., J. Am. Chem. Soc. 126:10500-10501 (2004).

(56) References Cited

OTHER PUBLICATIONS

Tsunoda et al., Tetrahedron Letters, 34(10): 1639-1642 (1993).
Van Maarseveen and Scheeren, Tetrahedron, 49(11):2325-2344 (1993).
Van Maarseveen et al., Tetrahedron, 51(16):4841-4852 (1995).
Wang et al., PNAS, 100(1):56-61 (2003).
Witus et al., J. Am. Chem. Soc., 132(47):16812-16817 (2010).
Wong et al., Chem. Rev., 109:4025-4053 (2009).
Wu et al., PNAS, 106(9): 3000-3005 (2009).
Yeom et al., Tetrahedron, 63:904-909 (2007).
Yi et al., Protein Chemistry, Angew. Chem. Int. Ed. 49:9417-9421 (2010).
Zeng et al., Nt. Methods, 6(3): 207-209 (2009).
Zheng et al., Synthesis, 9:1345-1350 (2008), first two pages only.
Pubchem 1H-indole-2-carbohydrazide, CID 231954, pp. 1-8, Create Date: Mar. 26, 2005 [retrieved on Feb. 20, 2014]. Retrieved from the Internet: <URL: http://pubchem.ncbi.nlm.nih.gov/summary/summary.cgi?cid=231954&loc=ec_rcs>; p. 1, 2D structure.
Pubchem CTK2E1080, CID 12343698, pp. 1-3, Create Date: Feb. 8, 2007 [retrieved on Feb. 6, 2014]. Retrieved from the Internet: <URL: http://pubchem.ncbi.nlm.nih.gov/summary/summary.cgi?cid=12343698&loc=ec_rcs>; p. 1, 20 structure.
Pubchem CID 12343703, pp. 1-2, Create Date: Feb. 8, 2007 [retrieved on Feb. 6, 2014]. Retrieved from the Internet: <URL: http://pubchem.ncbi.nlm.nih.gov/summary/summary.cgi?cid=12343703&loc=ec_rcs>; p. 1, 2D structure.
Pubchem SureCN743887, CID 66787168, pp. 1-2, Create Date: Nov. 30, 2012 [retrieved on Feb. 6, 2014]. Retrieved from the Internet: <URL: • • http://pubchem.ncbi.nlm.nih.gov/summary/summary.cgi?cid=66787168&loc=ec_rcs>; p. 1, 2D structure.
Agarwal, et al., PNAS, vol. 110, No. 1, pp. 46-51 (2013).

\* cited by examiner

PICTET-SPENGLER LIGATION FOR PROTEIN CHEMICAL MODIFICATION

CROSS-REFERENCE TO RELATED APPLICATIONS

The present application is a 371 National Stage entry of PCT/US2013/070421 which claims priority under 35 U.S.C. §119(e) to U.S. Provisional Patent Application No. 61/727,501 filed Nov. 16, 2012, both of which are incorporated herein by reference in their entireties.

STATEMENT AS TO RIGHTS TO INVENTIONS MADE UNDER FEDERALLY SPONSORED RESEARCH OR DEVELOPMENT

This invention was made with Government support under Grant No. GM59907 awarded by the National Institutes of Health. The Government has certain rights in the invention.

BACKGROUND OF THE INVENTION

Introduction

Reaction methodology for protein modification has been an active area of research for decades. Early strategies focused on global modification of native amino acids, providing access to heterogeneously modified products (Glazer A N (1970), "Specific Chemical Modification of Proteins," *Annu. Rev. Biochem.* 39(1): 101-130). However, a variety of applications necessitate site-specific modification of proteins: biophysical studies requiring knowledge of the site of attachment of a reporter molecule (Michalet X, Weiss S, & Jäger M (2006), "Single-Molecule Fluorescence Studies of Protein Folding and Conformational Dynamics," *Chem. Rev.* 106(5):1785-1813), preparation of protein microarrays and functional materials requiring immobilization in a specific orientation (Wong L S, Khan F, & Micklefield J (2009), "Selective Covalent Protein Immobilization: Strategies and Applications," *Chem. Rev.* 109(9):4025-4053), and conjugation of protein drugs with poly(ethylene glycol) or cytotoxic molecules, where the site of chemical modification affects the pharmacokinetic and therapeutic properties of the resulting biologic (Shen B-Q., et al. (2012), "Conjugation site modulates the in vivo stability and therapeutic activity of antibody-drug conjugates," *Nat. Biotechnol.* 30(2):184-189; Cho H, et al. (2011), "Optimized clinical performance of growth hormone with an expanded genetic code," *Proc. Natl. Acad. Sci. USA* 108(22):9060-9065). Therefore, in recent years, the field has developed methods to achieve sitespecific modification of proteins, typically involving the introduction of a nonnative functional group exhibiting bioorthogonal reactivity (Sletten E M & Bertozzi C R (2009), "Bioorthogonal Chemistry: Fishing for Selectivity in a Sea of Functionality," *Angew. Chem. Int. Ed.* 48(38):6974-6998; Stephanopoulos N & Francis M B (2011), "Choosing an effective protein bioconjugation strategy," *Nat. Chem. Biol.* 7(12):876-884).

Aldehydes and ketones are popular choices as chemical handles for site-specific protein modification. Their unique reactivity as mild electrophiles enables selective conjugation with α-effect nucleophiles such as substituted hydrazines and alkoxyamines, which generate hydrazone and oximeligated products, respectively (Jencks W P (1964), "Simple Carbonyl Group Reactions," *Prog. Phys. Org. Chem.* 2:63-128). A variety of chemical, enzymatic, and genetic methods have been developed to introduce aldehydes and ketones into proteins site-specifically. These include periodate oxidation of N-terminal serine or threonine residues (Geoghegan K F & Stroh J G (1992), "Site-Directed Conjugation of Nonpeptide Groups to Peptides and Proteins Via Periodate-Oxidation of a 2-Amino Alcohol-Application to Modification at N-Terminal Serine," *Bioconjugate Chem.* 3(2):138-146); pyridoxal phosphate-mediated N-terminal transamination to yield an α-ketoamide or glyoxamide (Gilmore J M, Scheck R A, Esser-Kahn A P, Joshi N S, & Francis M B (2006), "N-Terminal Protein Modification through a Biomimetic Transamination Reaction," *Angew. Chem. Int. Ed.* 45(32):5307-5311; Scheck R A, Dedeo M T, Iavarone A T, & Francis M B (2008), "Optimization of a Biomimetic Transamination Reaction," *J. Am. Chem. Soc.* 130(35):11762-11770; Witus L S. et al. (2010), "Identification of Highly Reactive Sequences For PLP-Mediated Bioconjugation Using a Combinatorial Peptide Library," *J. Am. Chem. Soc.* 132(47):16812-16817; Witus L S & Francis M (2009), "Site-Specific Protein Bioconjugation via a Pyridoxal 5'-Phosphate-Mediated N-Terminal Transamination Reaction," *Current Protocols in Chemical Biology*, (John Wiley & Sons, Inc); addition of ketone-containing small molecules to protein C-terminal thioesters generated by expressed protein ligation (Esser-Kahn A P & Francis M B (2008), "Protein-Cross-Linked Polymeric Materials through Site-Selective Bioconjugation," *Angew. Chem. Int. Ed.* 47(20):3751-3754); genetically encoded incorporation of unnatural amino acids containing ketones via amber stop codon suppression (Wang L, Zhang Z, Brock A, & Schultz P G (2003), "Addition of the keto functional group to the genetic code of Escherichia coli," *Proc. Natl. Acad. Sci. USA* 100(1):56-61; Hutchins B M. et al. (2011), "Selective Formation of Covalent Protein Heterodimers with an Unnatural Amino Acid," *Chem. Biol.* 18(3):299-303; Kim C H, et al. (2012), "Synthesis of Bispecific Antibodies using Genetically Encoded Unnatural Amino Acids," *J. Am. Chem. Soc.* 134(24):9918-9921); genetic encoding of peptide tags that direct enzymatic ligation of aldehyde- or ketone-bearing small molecules (Rashidian M, Song J M, Pricer R E, & Distefano M D (2012), "Chemoenzymatic Reversible Immobilization and Labeling of Proteins without Prior Purification," *J. Am. Chem. Soc.* 134(20):8455-8467; Chen I, Howarth M, Lin W, & Ting A Y (2005), "Site-specific labeling of cell surface proteins with biophysical probes using biotin ligase," *Nat. Methods* 2(2):99-104); and genetic encoding of a site for modification by the formylglycine generating enzyme (FGE), the "aldehyde tag" method developed in our lab (Carrico I S, Carlson B L, & Bertozzi C R (2007), "Introducing genetically encoded aldehydes into proteins," *Nat. Chem. Biol.* 3(6):321-322; Wu P. et al. (2009), "Site-specific chemical modification of recombinant proteins produced in mammalian cells by using the genetically encoded aldehyde tag," *Proc. Natl. Acad. Sci. USA* 106:3000-3005; Hudak J E, Yu H H, & Bertozzi C R (2011), "Protein Glycoengineering Enabled by the Versatile Synthesis of Aminooxy Glycans and the Genetically Encoded Aldehyde Tag," *J. Am. Chem. Soc.* 133(40):16127-16135); Hudak J E, et al. (2012), "Synthesis of Heterobifunctional Protein Fusions Using Copper-Free Click Chemistry and the Aldehyde Tag," *Angew. Chem. Int. Ed.* 51(17):4161-4165; Shi X. et al. (2012), "Quantitative fluorescence labeling of aldehyde-tagged proteins for single molecule imaging," *Nat. Methods* 9(5):499-503; Rabuka D, Rush J S, deHart G W, Wu P, & Bertozzi C R (2012), "Site-specific chemical protein conjugation using genetically encoded aldehyde tags," *Nat. Protoc.* 7(6):1052-1067).

The diversity of methods for introducing reactive carbonyl groups into proteins stands in contrast to the limited number of reactions that have been widely adopted for their chemical modification. The vast majority of reports use the hydrazone and oxime-forming reactions mentioned above, due to their bioorthogonality, operational simplicity (i.e., no auxiliary reagents are required), and good yields under mild aqueous conditions. However, the resulting C=N bonds are susceptible to hydrolysis (Mueller B M, Wrasidlo W A, & Reisfeld R A (1990), "Antibody conjugates with morpholinodoxorubicin and acid cleavable linkers," *Bioconjugate Chem.* 1(5):325-330), undermining their utility in situations where long-term stability is required. For example, it is believed that the lability of the hydrazone linkage in Mylotarg, an antibody-drug conjugate of α-CD33 with the cytotoxin calicheamicin, contributed to fatalities that led to withdrawal of the drug from the US market (Ducry L & Stump B (2009), "Antibody-Drug Conjugates: Linking Cytotoxic Payloads to Monoclonal Antibodies," *Bioconjugate Chem.* 21(1):5-13). The oxime has been identified as the most hydrolytically stable C=N linkage, but it is still thermodynamically unstable to hydrolysis under dilute conditions, decomposing via an acid-catalyzed process (Kalia J & Raines R T (2008), "Hydrolytic Stability of Hydrazones and Oximes," *Angew. Chem. Int. Ed.* 47(39):7523-7526). Many researchers have found that oxime conjugates that are kept under ideal storage conditions—low temperature, high concentration, and neutral or high pH—are kinetically stable and are therefore suitable for short-term laboratory studies (Hudak J E, Yu H H, & Bertozzi C R (2011), "Protein Glycoengineering Enabled by the Versatile Synthesis of Aminooxy Glycans and the Genetically Encoded Aldehyde Tag," *J. Am. Chem. Soc.* 133(40):16127-16135.); Shi X. et al. (2012), "Quantitative fluorescence labeling of aldehyde-tagged proteins for single-molecule imaging," *Nat. Methods* 9(5):499-503; Yi L, et al. (2010), "A Highly Efficient Strategy for Modification of Proteins at the C Terminus," *Angew. Chem. Int. Ed.* 49(49):9417-9421). However, biological applications requiring extended persistence of the conjugate at physiological temperatures and low concentrations necessitate a significantly more stable covalent linkage than the oxime provides.

The ideal bioconjugation reaction would form a stable C—C bond with protein aldehydes and ketones. A few such reactions have been reported, but they are limited by slow reaction kinetics (Sasaki T, Kodama K, Suzuki H, Fukuzawa S, & Tachibana K (2008), "N-terminal labeling of proteins by the Pictet-Spengler reaction," *Bioorg. Med. Chem. Lett.* 18(16):4550-4553) or the need for organic cosolvents (Alam J, Keller T H, & Loh T-P (2010), "Functionalization of Peptides and Proteins by Mukaiyama Aldol Reaction," *J. Am. Chem. Soc.* 132(28):9546-9548; Alam J, Keller T H, & Loh T-P (2011), "Indium mediated allylation in peptide and protein functionalization," *Chem. Commun.* 47(32):9066-9068). A C—C bond forming transformation possessing the kind of generality and operational simplicity that led to the widespread adoption of oxime bioconjugation has not yet been reported. Such a technique would represent a significant advance in the art. Surprisingly, the present invention provides an entry into reagents and methods based upon this technique and conjugates of biomolecules formed thereby.

BRIEF SUMMARY OF THE INVENTION

In various embodiments, the present invention provides compounds able to participate in the Pictet-Spengler ligation, a C—C bond forming reaction that capitalizes on the bioorthogonality of oxime formation in an intermediate step. This new reaction is of use to prepare hydrolytically stable conjugates with biomolecules, e.g., glyoxal- and formylglycine-modified proteins, including antibodies.

The Pictet-Spengler ligation possesses the selectivity, kinetics, and operational simplicity that originally popularized traditional oxime- and hydrazone protein conjugation reactions. However, its oxacarboline product enables the persistence of bioconjugates in hydrolytically demanding environments where C=N linkages currently fail. We demonstrated the generality of the method using a variety of aldehyde-functionalized proteins, including a therapeutically relevant human IgG. Model reactions suggest that ketones are potential substrates as well, a future direction to explore with respect to bioconjugation. We focused here on the use of the Pictet-Spengler ligation for modification of purified proteins, but applications extend to other biomolecules that are amenable to functionalization with reactive carbonyl groups. Methods for metabolic (Mahal L K, Yarema K J, & Bertozzi C R (1997), "Engineering Chemical Reactivity on Cell Surfaces Through Oligosaccharide Biosynthesis," *Science* 276(5315):1125-1128; Sadamoto R, et al. (2004), "Control of Bacteria Adhesion by Cell-Wall Engineering," *J. Am. Chem. Soc.* 126(12):3755-3761; Hang H C & Bertozzi C R (2001), "Ketone Isosteres of 2-N-Acetamidosugars as Substrates for Metabolic Cell Surface Engineering," *J. Am. Chem. Soc.* 123(6):1242-1243), enzymatic (Tai H-C, Khidekel N, Ficarro S B, Peters E C, & Hsieh-Wilson L C (2004), "Parallel Identification of O-GlcNAc-Modified Proteins from Cell Lysates," *J. Am. Chem. Soc.* 126(34):10500-10501), and chemical (O'Shannessy D J, Voorstad P J, & Quarles R H (1987), "Quantitation of glycoproteins on electroblots using the biotin-streptavidin complex," *Anal. Biochem.* 163(1):204-209; Zeng Y, Ramya T N C, Dirksen A, Dawson P E, & Paulson J C (2009), "High-efficiency labeling of sialylated glycoproteins on living cells," *Nat. Methods* 6(3):207-209) functionalization of glycans with ketone and aldehyde groups are well-established, and are finding use in proteomic analyses of glycosylated proteins. The Pictet-Spengler ligation may enhance the performance of these methods, as well as others that seek to detect or manipulate carbonyl groups using bioorthogonal chemistry (Smith C D, et al. (1991), "Excess brain protein oxidation and enzyme dysfunction in normal aging and in Alzheimer disease," *Proc. Natl. Acad. Sci. USA* 88(23): 10540-10543; Nystrom T (2005), "Role of oxidative carbonylation in protein quality control and senescence," *EMBO J* 24(7):1311-1317).

In an exemplary embodiment, the invention provides a compound having the formula:

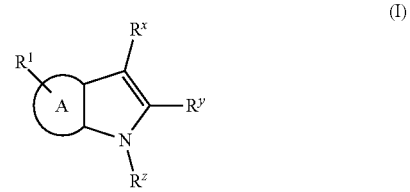

(I)

wherein A is present or absent and, when present, is a substituted or unsubstituted aryl or substituted or unsubstituted heteroaryl moiety and $R^1$ is a member selected from H, substituted or unsubstituted alkyl, substituted or unsubstituted heteroalkyl, substituted or unsubstituted aryl, substituted or unsubstituted heteroaryl, halogen, CN, $CF_3$, acyl, —SO$_2$NR$^5$R$^6$, —NR$^5$R$^6$, —OR$^5$, —S(O)$_2$R$^5$, —C(O)R$^5$, —COOR$^5$, —CONR$^5$R$^6$, —S(O)$_2$OR$^5$, —OC(O)R$^5$, —C(O)NR$^5$R$^6$, —NR$^5$C(O)R$^6$, —NR$^5$SO$_2$R$^6$ and —NO$_2$, wherein two or more of R$^1$, R$^2$, R$^3$, and R$^4$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

R$^5$ and R$^6$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and R$^9$ and R$^{10}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

The symbols R$^x$, R$^y$ and R$^z$ represent H, substituted or unsubstituted alkyl or substituted or unsubstituted heteroalkyl, with the proviso that at least one of R$^x$ and R$^y$ has a formula selected from:

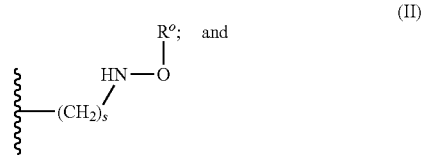

(II)

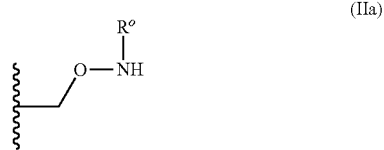

(IIa)

R$^o$ is selected from H, substituted or unsubstituted alkyl and substituted or unsubstituted heteroalkyl; and s is selected from 1 and 2. A member selected from R$^1$, R$^x$, R$^y$ and R$^z$ has the formula:

(III)

wherein L is a linker selected from substituted or unsubstituted alkyl and substituted or unsubstituted heteroalkyl; and X is selected from a detectable label, a crosslinking moiety, poly(alkylene oxide) and an affinity label.

In another exemplary embodiment, the invention provides a method of forming a conjugate of a biomolecule (e.g., an antibody) using a compound of the invention, e.g., a compound of Formula I.

In various embodiments, the invention provides biomolecule conjugates formed by reaction between a protein and a compound of Formula I.

In an exemplary embodiment, the invention provides assays for biomolecules utilizing a conjugate formed between a protein and a compound according to Formula I. The method includes forming a conjugate between a biomolecule and a compound of the invention and detecting the conjugate.

Other exemplary objects, advantages and aspects of the invention are set forth in the detailed description that follows.

DETAILED DESCRIPTION OF THE INVENTION

I. Introduction

Figures 1A, 1B, 1C, 1D:
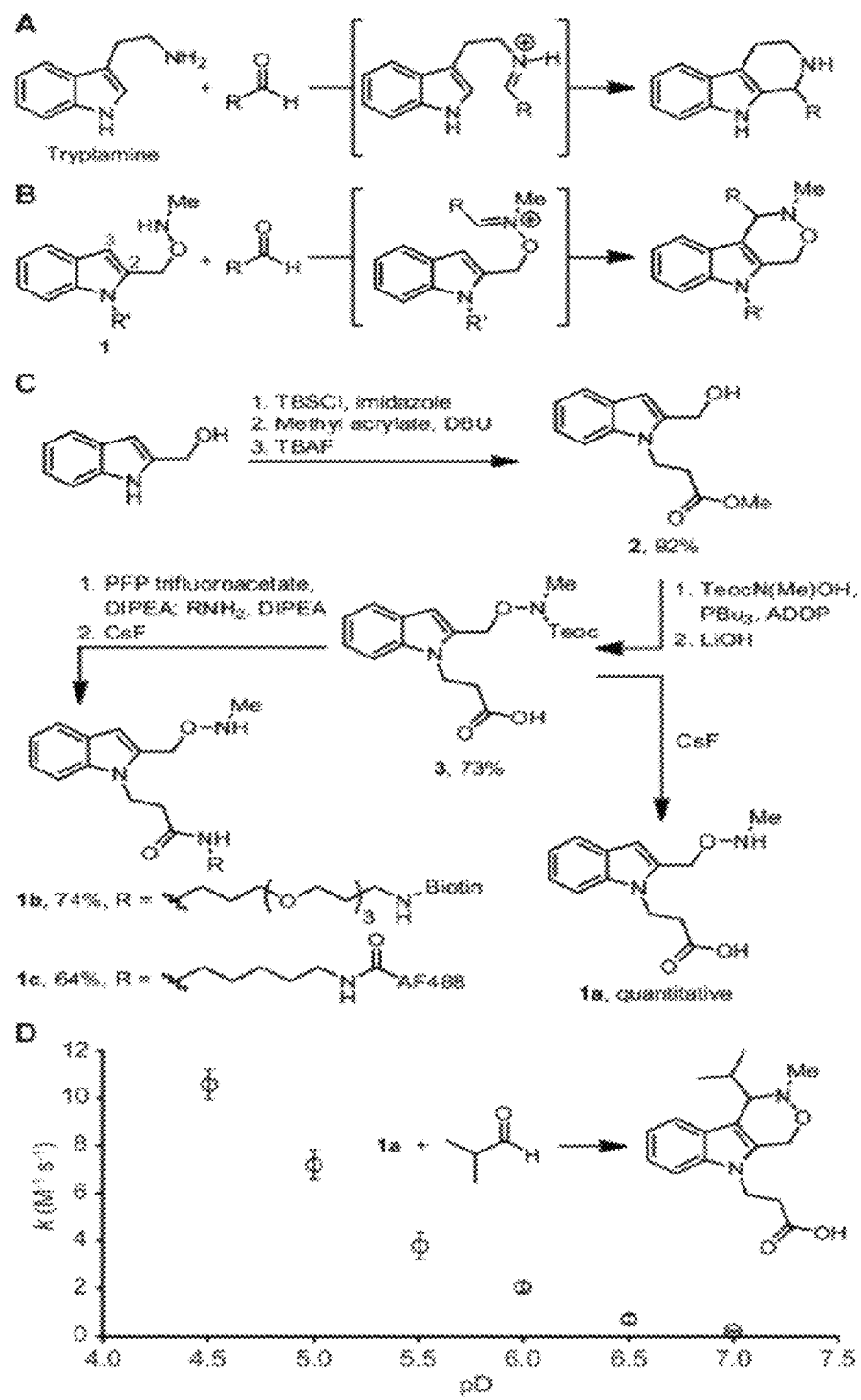
FIG. 1A-FIG. 1D is a design and evaluation of the Pictet-Spengler ligation. (A) The Pictet-Spengler reaction. (B) The Pictet-Spengler ligation. (C) Synthesis of aldehyde- and ketone-reactive indoles used in this study. (D) Second-order rate constants for the reaction of 1a with isobutyraldehyde in D$_2$O solutions containing 100 mM deuterated acetate (pD≤5.5) or phosphate (pD≥6.0) buffers. Error bars represent standard deviation of at least three replicate experiments. Abbreviations used: TBS, tert-butyldimethylsilyl; DBU, 1,8-diazabicyclo[5.4.0]undec-7-ene; TBAF, tetrabutylammonium fluoride; Teoc, 2-(trimethylsilyl)ethoxycarbonyl; ADDP, 1,1'-(azodicarbonyl)dipiperidine; PFP, pentafluorophenyl; DIPEA, diisopropylethylamine FIG. 2A

Novel methods for preferentially producing target protein conjugates are provided by the invention. In exemplary embodiments, these conjugates are formed between a protein and a detectable label or an affinity label. The compounds and methods of the invention represent a complete system for both producing and identifying labeled proteins. In an exemplary embodiment, the protein conjugates preferentially bind to a macromolecular target or target site. Exemplary target proteins include a variety of cellular- and non-cellular-associated molecules.

Before the invention is described in greater detail, it is to be understood that the invention is not limited to particular embodiments described herein as such embodiments may vary. It is also to be understood that the terminology used herein is for the purpose of describing particular embodiments only, and the terminology is not intended to be limiting. The scope of the invention will be limited only by the appended claims. Unless defined otherwise, all technical and scientific terms used herein have the same meaning as commonly understood by one of ordinary skill in the art to which this invention belongs. Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. All publications, patents, and patent applications cited in this specification are incorporated herein by reference to the same extent as if each individual publication, patent, or patent application were specifically and individually indicated to be incorporated by reference. Furthermore, each cited publication, patent, or patent application is incorporated herein by reference to disclose and describe the subject matter in connection with which the publications are cited. The citation of any publication is for its disclosure prior to the filing date and should not be construed as an admission that the invention described herein is not entitled to antedate such publication by virtue of prior invention. Further, the dates of publication provided might be different from the actual publication dates, which may need to be independently confirmed.

It is noted that the claims may be drafted to exclude any optional element. As such, this statement is intended to serve as antecedent basis for use of such exclusive terminology as "solely," "only," and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the invention. Any recited method may be carried out in the order of events recited or in any other order that is logically possible. Although any methods and materials similar or equivalent to those described herein may also be used in the practice or testing of the invention, representative illustrative methods and materials are now described.

In describing the present invention, the following terms will be employed, and are defined as indicated below.

II. Definitions

Where substituent groups are specified by their conventional chemical formulae, written from left to right, the structures optionally also encompass the chemically identical substituents, which would result from writing the structure from right to left, e.g., —$CH_2O$— is intended to also optionally recite —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals (e.g., alkylene), having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9\text{-}10}$, oleoyl chain or the diunsaturated $C_{9\text{-}10, 12\text{-}13}$ linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "aryloxy" and "heteroaryloxy" are used in their conventional sense, and refer to those aryl or heteroaryl groups attached to the remainder of the molecule via an oxygen atom.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —$CO_2R'$— represents both —C(O)OR' and —OC(O)R'.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 4 rings), which are fused together or linked covalently. The term "heteroaryl" refers to aryl groups (or rings) that contain from one to four heteroatoms selected from N, O, S, Si, Se, P and B, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to optionally include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R'', R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R'', R''' and R''''groups when more than one of these groups is present. When R' and R'' are attached to the same nitrogen atom, they can be combined with the nitrogen atom to form a 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents", which are components of exemplary "substituted alkyl" and "substituted heteroalkyl" moieties.

Similar to the substituents described for the alkyl radical, substituents for the aryl and heteroaryl groups are generically referred to as "aryl group substituents." The substituents are selected from, for example: H, substituted or unsubstituted alkyl, substituted or unsubstituted aryl, substituted or unsubstituted heteroaryl, substituted or unsubstituted heterocycloalkyl, —OR', =O, =NR', =N—OR', —NR'R'', —SR', -halogen, —SiR'R''R''', —OC(O)R', —C(O)R', —CO$_2$R', —CONR'R'', —OC(O)NR'R'', —NR''C(O)R', —NR'—C(O)NR''R''', —NR''C(O)$_2$R', —NR—C(NR'R''R''')=NR'''', —NR—C(NR'R'')=NR''', —S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R'', R''' and R''''are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR''R''')$_d$—, where s and d are independently integers from 0 to 3, and X is —O—, —NR'—, —S—, —S(O)—, —S(O)$_2$—, or —S(O)$_2$NR'—. The substituents R, R', R'' and R''' are preferably independently selected from hydrogen or substituted or unsubstituted (C$_1$-C$_6$)alkyl. These terms encompass groups considered exemplary "aryl group substituents", which are components of exemplary "substituted aryl" and "substituted heteroaryl" moieties.

As used herein, the term "acyl" describes a substituent containing a carbonyl residue, C(O)R. Exemplary species for R include H, halogen, substituted or unsubstituted alkyl, substituted or unsubstituted aryl, substituted or unsubstituted heteroaryl, and substituted or unsubstituted heterocycloalkyl.

As used herein, the term "fused ring system" means at least two rings, wherein each ring has at least 2 atoms in common with another ring. "Fused ring systems may include aromatic as well as non-aromatic rings. Examples of "fused ring systems" are naphthalenes, indoles, quinolines, chromenes and the like.

As used herein, the term "heteroatom" includes oxygen (O), nitrogen (N), sulfur (S) and silicon (Si) and boron (B).

"Poly(alkylene oxide)" refers to a genus of compounds having a polyether backbone. Poly(alkylene oxide) species of use in the present invention include, for example, straight- and branched-chain species. Moreover, exemplary poly(alkylene oxide) species can terminate in one or more reactive, activatable, or inert groups. For example, poly(ethylene glycol) is a poly(alkylene oxide) consisting of repeating ethylene oxide subunits, which may or may not include additional reactive, activatable or inert moieties at either terminus Useful poly(alkylene oxide) species include those in which one terminus is "capped" by an inert group, e.g., monomethoxy-poly(alkylene oxide). When the molecule is a branched species, it may include multiple reactive, activatable or inert groups at the termini of the alkylene oxide chains and the reactive groups may be either the same or different. Derivatives of straight-chain poly(alkylene oxide) species that are heterobifunctional are also known in the art.

"Protein" refers to a polymer in which the monomers are amino acids and are joined together through amide bonds, alternatively referred to as a polypeptide. Additionally, unnatural amino acids, for example, β-alanine, phenylglycine and homoarginine are also included Amino acids that are not nucleic acid-encoded may also be incorporated into proteins. Furthermore, amino acids that have been modified to include reactive groups, glycosylation sites, polymers, therapeutic moieties, biomolecules and the like may also be used in the invention. Amino acids may be either the D- or L-isomer thereof. The L-isomer is generally preferred. As used herein, "protein" refers to both glycosylated and unglycosylated polypeptides. Also included are proteins that are incompletely glycosylated by a system that expresses the protein. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, New York; Houston et al., 1988, Proc. Natl. Acad. Sci. USA 85:5879-5883; Bird et al., 1988, Science 242:423-426). "Antibodies" also encompasses synthetic antibodies.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The terms "substrate" and "precursor" are used interchangeably and refer to a biomolecule, which is able to be chemically modified with a moiety that includes an aldehyde or ketone.

The compounds disclosed herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

"Affinity Label": As used herein, the term affinity label refers to a group, moiety, or entity that specifically interacts/associates with a counterpart entity (e.g., capture agent). The affinity label/capture agent pair is often referred to as an "affinity pair". The affinity pair may be a biochemical pair. Non-limiting examples of biochemical pairs include antibody-antigen, enzyme-inhibitor, hormone-receptor, sugar-lectin, biotin-(strept)avidin and complementary nucleic acid components.

"Associated with" or "Associate with": When two entities are associated with or associate with one another, as described herein, they are linked by a direct or indirect covalent or non-covalent interaction. Preferably, the association is covalent. Desirable non-covalent interactions include hydrogen bonding, van der Waals interactions, hydrophobic interactions, magnetic interactions, electrostatic interactions, affinity interactions or combinations thereof, etc.

A "detectable label" or a "detectable moiety" is a composition detectable by spectroscopic, photochemical, biochemical, immunochemical, chemical, or other physical means. For example, labels suitable for use in the present invention include, for example, radioactive labels (e.g., $^{32}$P), fluorophores (e.g., fluorescein), electron dense reagents, enzymes (e.g., as commonly used in an ELISA), biotin, digoxigenin, or haptens and proteins which are made detectable, e.g., by incorporating a radiolabel into the hapten or peptide, or used to detect antibodies specifically reactive with the hapten or peptide.

The invention is further illustrated by reference to compounds that undergo Pictet-Spengler ligation with protein-bound carbonyl moieties, e.g., aldehydes and ketones.

III. The Compositions

In an exemplary embodiment, the invention provides a compound having the formula:

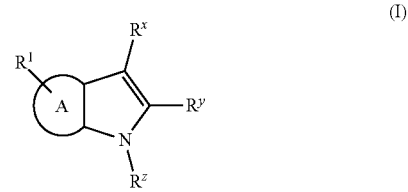

(I)

wherein A is present or absent and, when present, is a substituted or unsubstituted aryl or heteroaryl moiety and $R^1$ is a member selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^5R^6$, $-NR^5R^6$, $-OR^5$, $-S(O)_2R^5$, $-C(O)R^5$, $-COOR^5$, $-CONR^5R^6$, $-S(O)_2OR^5$, $-OC(O)R^5$, $-C(O)NR^5R^6$, $-NR^5C(O)R^6$, $-NR^5SO_2R^6$ and $-NO_2$, wherein two or more of $R^1$, $R^2$, $R^3$, and $R^4$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl. The symbols $R^x$, $R^y$ and $R^z$ represent H, substituted or unsubstituted alkyl or substituted or unsubstituted heteroalkyl, with the proviso that at least one of $R^x$ and $R^y$ has a formula selected from:

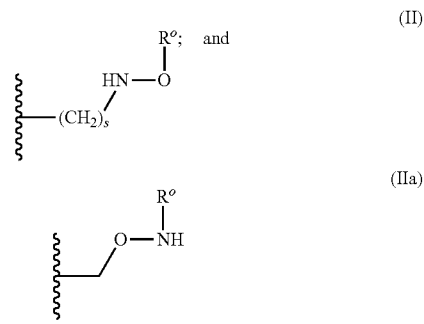

(II)

(IIa)

$R^o$ is selected from H, substituted or unsubstituted alkyl and substituted or unsubstituted heteroalkyl; and s is selected from 1 and 2. A member selected from $R^1$, $R^x$, $R^y$ and $R^z$ has the formula:

(III)

wherein L is a linker selected from substituted or unsubstituted alkyl and substituted or unsubstituted heteroalkyl; and X is selected from a detectable label, a crosslinking moiety, poly(alkylene oxide) and an affinity label.

In an exemplary embodiment, the L-X cassette is bound to the nitrogen of the ring structure, providing a compound having the formula:

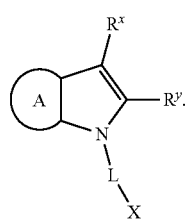

In various embodiments, the compounds of the invention have a formula selected from:

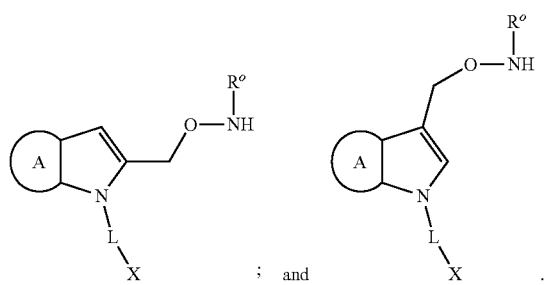

In an exemplary embodiment, the compounds of the invention have a formula selected from:

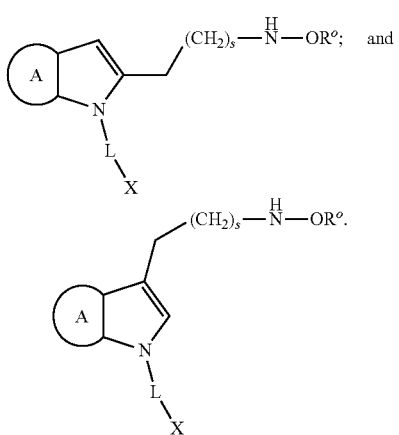

In various embodiments, A is substituted or unsubstituted phenyl.

In various embodiments, the compounds of the invention have the formula:

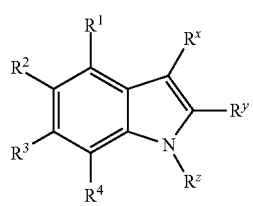

in which $R^1$, $R^2$, $R^3$, and $R^4$ are selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^5R^6$, $-NR^5R^6$, $-OR^5$, $-S(O)_2R^5$, $-C(O)R^5$, $-COOR^5$, $-CONR^5R^6$, $-S(O)_2OR^5$, $-OC(O)R^5$, $-C(O)NR^5R^6$, $-NR^5C(O)R^6$, $-NR^5SO_2R^6$ and $-NO_2$, wherein two or more of $R^1$, $R^2$, $R^3$, and $R^4$, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl.

$R^5$ and $R^6$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl, and $R^9$ and $R^{10}$, together with the atoms to which they are bonded, are optionally joined to form a 5- to 7-membered ring which is a member selected from substituted or unsubstituted cycloalkyl, substituted or unsubstituted heterocycloalkyl, substituted or unsubstituted aryl and substituted or unsubstituted heteroaryl.

As used herein, the term "linker," refers to constituents of the compounds of the invention joining X to the remainder of the molecule. Spacers can be hydrophilic (e.g., tetraethylene glycol, hexaethylene glycol, polyethylene glycol) or they can be hydrophobic (e.g., hexane, decane, etc.) or hybrid structures included both hydrophilic and hydrophobic domains.

In an exemplary embodiment, the compound of the invention includes a linker selected from $C_1$-$C_{30}$ alkyl or heteroalkyl groups, $C_1$-$C_{30}$ substituted alkyl or heteroalkyl groups, polyols, polyethers (e.g., poly(ethyleneglycol)), polyamines, polyamino acids, polysaccharides and combinations thereof. In various embodiments, the linker, L, is substituted or unsubstituted alkyl having 1, 2, 3, 4, 5, 6, 7, 8, 9 or 10 carbon atoms.

In various embodiments, the linker has the formula:

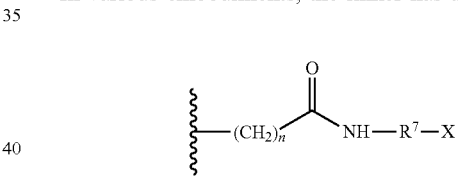

wherein $R^7$ is a selected from substituted or unsubstituted alkyl and substituted or unsubstituted heteroalkyl; and n is selected from 0, 1, 2, 3, 4, 5, 6, 7, 8, 9 and 10.

In various embodiments, the linker comprises a poly (alkylene oxide) subunit comprising the formula:

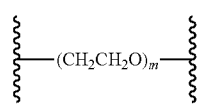

in which m is a selected from 1, 2, 3, 4, 5, 6, 7, 8, 9 or 10.

In various embodiments, the linker includes the poly (alkylene oxide) subunit:

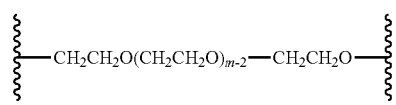

In certain embodiments, it is advantageous to have a linker of the compound of the invention impart flexibility and distance to the attachment between X and the remainder of the molecule. In various embodiments, using linker groups, the properties of X and or of the entire compound are modulated.

In an exemplary embodiment, the spacer serves to distance the compound of the invention from a biomolecule with which it is to be reacted. Linkers with this characteristic have several uses, including reducing steric interference between X and an incoming biomolecule.

In yet a further embodiment, a linker group used in the compounds of the invention is provided with a group that can be cleaved to release X (and optionally a moiety, e.g., a molecule bound to an affinity label), fluorophore, poly (alkylene oxide), and the like from the conjugate. Many cleaveable groups are known in the art. See, for example, Jung et al., *Biochem. Biophys. Acta,* 761: 152-162 (1983); Joshi et al., *J. Biol. Chem.,* 265: 14518-14525 (1990); Zarling et al., *J. Immunol.,* 124: 913-920 (1980); Bouizar et al., *Eur. J. Biochem.,* 155: 141-147 (1986); Park et al., *J. Biol. Chem.,* 261: 205-210 (1986); Browning et al., *J. Immunol.,* 143: 1859-1867 (1989). Moreover, a broad range of cleavable, bifunctional (both homo- and hetero-bifunctional) spacer arms are commercially available from suppliers such as Pierce, and many of these are appropriate for incorporation into the compounds of the invention.

One of the advantages of the compounds of the invention is that they can be used with a wide range of energy donor and/or acceptor molecules to construct probes. A vast array of fluorophores useful in conjunction with the PLs are known to those of skill in the art. See, for example, Cardullo et al., *Proc. Natl. Acad. Sci. USA* 85: 8790-8794 (1988); Dexter, D. L., *J. of Chemical Physics* 21: 836-850 (1953); Hochstrasser et al., *Biophysical Chemistry* 45: 133-141 (1992); Selvin, P., *Methods in Enzymology* 246: 300-334 (1995); Steinberg, I. *Ann. Rev. Biochem.,* 40: 83-114 (1971); Stryer, L. *Ann. Rev. Biochem.,* 47: 819-846 (1978); Wang et al., *Tetrahedron Letters* 31: 6493-6496 (1990); Wang et al., *Anal. Chem.* 67: 1197-1203 (1995).

A non-limiting list of exemplary fluorophore that can be used in conjunction with the quenchers of the invention is provided in Table 1.

TABLE 1

4-acetamido-4'-isothiocyanatostilbene-2,2'disulfonic acid
acridine and derivatives:
    acridine
    acridine isothiocyanate
5-(2'-aminoethyl)aminonaphthalene-1-sulfonic acid (EDANS)
4-amino-N-[3-vinylsulfonyl)phenyl]naphthalimide-3,5 disulfonate
N-(4-anilino-1-naphthyl)maleimide
anthranilamide
BODIPY
Brilliant Yellow
coumarin and derivatives:
    coumarin
        7-amino-4-methylcoumarin (AMC, Coumarin 120)
        7-amino-4-trifluoromethylcouluarin (Coumaran 151)
cyanine dyes
cyanosine
4',6-diaminidino-2-phenylindole (DAPI)
5',5''-dibromopyrogallol-sulfonaphthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansylchloride)
4-(4'-dimethylaminophenylazo)benzoic acid (DABCYL)
4-dimethylaminophenylazophenyl-4'-isothiocyanate (DABITC)
eosin and derivatives:
    eosin
    eosin isothiocyanate TABLE 1-continued erythrosin and derivatives:
    erythrosin B
    erythrosin isothiocyanate
ethidium
fluorescein and derivatives:
    5-carboxyfluorescein (FAM)
    5-(4,6-dichlorotriazin-2-yl)aminofluorescein (DTAF)
    2',7'-dimethoxy-4'5'-dichloro-6-carboxyfluorescein (JOE)
    fluorescein
    fluorescein isothiocyanate
    QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:
    pyrene
    pyrene butyrate
    succinimidyl 1-pyrene butyrate
quantum dots
Reactive Red 4 (Cibacron™ Brilliant Red 3B-A)
rhodamine and derivatives:
    6-carboxy-X-rhodamine (ROX)
    6-carboxyrhodamine (R6G)
    lissamine rhodamine B sulfonyl chloride rhodamine (Rhod)
    rhodamine B
    rhodamine 123
    rhodamine X isothiocyanate
    sulforhodamine B
    sulforhodamine 101
sulfonyl chloride derivative of sulforhodamine 101 (Texas Red)
N,N,N',N'-tetramethyl-6-carboxyrhodamine (TAMRA)
tetramethyl rhodamine
    tetramethyl rhodamine isothiocyanate (TRITC)
riboflavin
rosolic acid
lanthanide chelate derivatives There is a great deal of practical guidance available in the literature for selecting appropriate fluorophores for particular probes, as exemplified by the following references: Pesce et al., Eds., FLUORESCENCE SPECTROSCOPY (Marcel Dekker, New York, 1971); White et al., FLUORESCENCE ANALYSIS: A PRACTICAL APPROACH (Marcel Dekker, New York, 1970); and the like. The literature also includes references providing exhaustive lists of fluorescent and chromogenic molecules and their relevant optical properties (see, for example, Berlman, HANDBOOK OF FLUORESCENCE SPECTRA OF AROMATIC MOLECULES, 2nd Edition (Academic Press, New York, 1971); Griffiths, COLOUR AND CONSTITUTION OF ORGANIC MOLECULES (Academic Press, New York, 1976); Bishop, Ed., INDICATORS (Pergamon Press, Oxford, 1972); Haugland, HANDBOOK OF FLUORESCENT PROBES AND RESEARCH CHEMICALS (Molecular Probes, Eugene, 1992) Pringsheim, FLUORESCENCE AND PHOSPHORESCENCE (Interscience Publishers, New York, 1949); and the like. Further, there is extensive guidance in the literature for derivatizing reporter and quencher molecules for covalent attachment via readily available reactive groups that can be added to a molecule.

The diversity and utility of chemistries available for conjugating fluorophores to other molecules and surfaces is exemplified by the extensive body of literature on preparing nucleic acids derivatized with fluorophores. See, for example, Haugland (supra); Ullman et al., U.S. Pat. No. 3,996,345; Khanna et al., U.S. Pat. No. 4,351,760.

In another exemplary embodiment, X is a chelator or chelate. Exemplary chelators are aminocarboylates (i.e.

EDTA, DTPA, DOTA, NTA, HDTA, etc. and their phosphonate analogs such as DTPP, EDTP, HDTP, NTP, etc).

Many useful chelating groups, crown ethers, cryptands and the like are known in the art and can be incorporated into the compounds of the invention. See, for example, Pitt et al., "The Design of Chelating Agents for the Treatment of Iron Overload," In, INORGANIC CHEMISTRY IN BIOLOGY AND MEDICINE; Martell, Ed.; American Chemical Society, Washington, D.C., 1980, pp. 279-312; Lindoy, THE CHEMISTRY OF MACROCYCLIC LIGAND COMPLEXES; Cambridge University Press, Cambridge,1989; Dugas, BIOORGANIC CHEMISTRY; Springer-Verlag, New York, 1989, and references contained therein.

Additionally, a manifold of routes allowing the attachment of chelating agents, crown ethers and cyclodextrins to other molecules is available to those of skill in the art. See, for example, Meares et al., "Properties of In Vivo Chelate-Tagged Proteins and Polypeptides." In, MODIFICATION OF PROTEINS: FOOD, NUTRITIONAL, AND PHARMACOLOGICAL ASPECTS;" Feeney, et al., Eds., American Chemical Society, Washington, D.C., 1982, pp. 370-387; Kasina et al., *Bioconjugate Chem.*, 9: 108-117 (1998); Song et al., *Bioconjugate Chem.*, 8: 249-255 (1997).

In other embodiments X is a fluorescence sensitizer. Exemplary sensitizers include rhodamine 560, 575 and 590 fluoresceins, 2- or 4-quinolones, 2 or 4-coumarins, or derivatives thereof e.g. coumarin 445, 450, 490, 500 and 503, 4-trifluoromethylcoumarin (TFC), 7-diethyl-amino-cumarin-3-carbohyddzide, etc., and especially carbostyril 124 (7-amino-4-methyl-2-quinolone), coumarin 120 (7-amino-4-methyl-2-coumarin), coumarin 124 (7-amino-4-(trifluoromethyl)-2-coumarin), aminomethyltrimethylpsoralen, napthalene and the like.

In an exemplary embodiment, the sensitizer is a moiety that comprises a napthyl moiety.

In another embodiment, X is an affinity moiety. Exemplary affinity moieties are selected from a wide range of small bioactive molecules (e.g., drugs, pesticides, toxins, etc.), organic functional groups (e.g., amines, carbonyls, carboxylates, etc.), biomolecules, metals, metal chelates and organometallic compounds.

Methods and compositions are provided for producing oligomeric affinity label molecules and preferentially covalently bonding those oligomeric affinity label molecules to a macromolecular target, where the target is a member of a complex mixture, i.e., such as serum, blood, cerebral spinal fluid, etc., and/or there is preferential bonding at one or a limited number of a plurality of bonding sites on the macromolecular target. The methods described herein represent a complete system for both producing and identifying affinity label molecules from a combinatorial library which preferentially bind to a macromolecular target or target site and preferentially binding those affinity labels to a macromolecule of interest either ex vivo or in vivo.

Exemplary affinity label molecules of use this invention will be oligomeric and have an available reactive functional group with a reactivity complementary to that of a reactive functional group on linker moiety, L. Exemplary affinity label molecules have the ability to specifically interact with a macromolecular target or target site of interest in a complex mixture. By specifically interacting with a macromolecular target or target site is meant that the affinity label will exhibit some preferential binding to the macromolecular target as against other components in the environment in which the affinity label molecule and the macromolecular target will be combined. The preference will normally be at least about 1.5, preferably at least about 2 times, random binding in the absence of the oligomer.

In exemplary embodiments, the affinity label is an oligomeric affinity label. The oligomeric affinity label may be an oligopeptide, oligonucleotide, oligosaccharide, combinations thereof, or the like.

Generally, the number of monomeric units in each oligomeric affinity label will be from 4 to 12, more usually from 4 to 8 and preferably from 5 to 8. The monomer units comprising the oligomeric affinity label may be naturally occurring or synthetic, generally being from about 2 to 30 carbon atoms, usually from about 2 to 18 carbon atoms and preferably from about 2 to 12 carbon atoms.

In various embodiments, the affinity label is an oligopeptide, and the amino acid monomers may be naturally occurring or synthetic. Conveniently, the naturally occurring L-a-amino acids will be used, although the D-enantiomers may also be employed.

In various embodiments, the affinity label is an oligonucleotide. Oligonucleotides, either naturally occurring or synthetic nucleotide monomers are easily employed.

Particularly, for synthetic nucleotides, the phosphate or sugar groups may be modified where phosphate may be substituted by having the oxygen atoms replaced with sulfur or nitrogen, the phosphate group may be replaced with sulfonate, amide etc., the ribose or deoxyribose may be replaced with 5 to 6 carbon atom sugars such as arabinose, fructose, glucose, or the like, and the purines and pyrimidines may be modified by substitution on nitrogen, with alkyl or acyl, may employ different ring structures, may have nitrogen replaced by oxygen, or vice versa, and the like.

In various embodiments the affinity label is an oligosaccharide. An exemplary oligosaccharide will usually have from 4 to 6 monomeric units which may be linear or branched, comprised of sugars of from 5 to 8 carbon atoms. Various modifications of known oligosaccharides may be employed, particularly where one is interested in binding to lectins or adhesion molecules.

In another exemplary embodiment, X is a drug moiety. The drug moieties can be agents already accepted for clinical use or they can be drugs whose use is experimental, or whose activity or mechanism of action is under investigation. The drug moieties can have a proven action in a given disease state or can be only hypothesized to show desirable action in a given disease state. In another exemplary embodiment, the drug moieties are compounds being screened for their ability to interact with an analyte of choice. Drug moieties useful as X in the instant invention include drugs from a broad range of drug classes having a variety of pharmacological activities.

In still further exemplary embodiments, X is a biomolecule such as a protein, nucleic acid, peptide or an antibody. Biomolecules useful in practicing the present invention can be derived from any source. The biomolecules can be isolated from natural sources or can be produced by synthetic methods. Proteins can be natural proteins or mutated proteins. Mutations can be effected by chemical mutagenesis, site-directed mutagenesis or other means of inducing mutations known to those of skill in the art. Proteins useful in practicing the instant invention include, for example, enzymes, antigens, antibodies and receptors. Antibodies can be either polyclonal or monoclonal. Peptides and nucleic acids can be isolated from natural sources or can be wholly or partially synthetic in origin.

In those embodiments in which X is a protein or antibody, the protein joined to the rest of the molecule through any reactive peptide residue available on the surface of the protein. In preferred embodiments, the reactive groups are amines or carboxylates. In exemplary embodiments, the reactive groups are the ε-amine groups of lysine residues.

Other exemplary affinity moieties include, without limitation, minor groove binders, and intercalating agents.

IV. The Methods

The present invention also provides methods of preparing a conjugate between a biomolecule and a compound of the invention. In an exemplary embodiment, there is provided a method of modifying a biomolecule functionalized with a member selected from an aldehyde and a ketone, said method comprising: (a) contacting said biomolecule with a compound according to any preceding claim under reaction conditions appropriate to form a cyclized Pictet-Spengler adduct by reaction of the compound with a moiety selected from the aldehyde and the ketone, thereby modifying said biomolecule.

In an exemplary embodiment, the invention provides a method of activating a biomolecule precursor for reaction with a compound of the invention. Thus, prior to step (a), a precursor biomolecule is modified with a reactive moiety comprising a member selected from said aldehyde and said ketone, thereby forming the biomolecule functionalized with a member selected from an aldehyde and a ketone.

V. The Conjugates

The invention also provides conjugates formed between the compounds of the invention and a biomolecule. Exemplary biomolecule components of the conjugates of the invention include protein, a glycan, a nucleic acid, a metabolite, an inhibitor, a lipid, and a cofactor.

In an exemplary embodiment, the conjugate has a formula selected from:

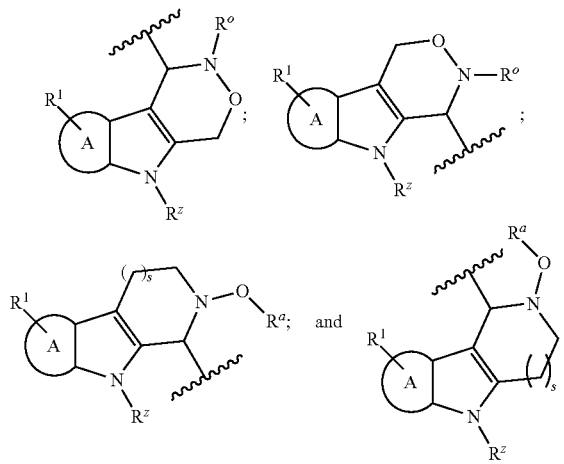

in which $R^1$, $R^5$ and $R^6$ are as discussed above.

In various embodiments, the conjugates have a formula which is a member selected from:

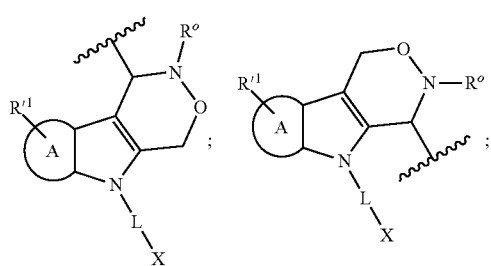

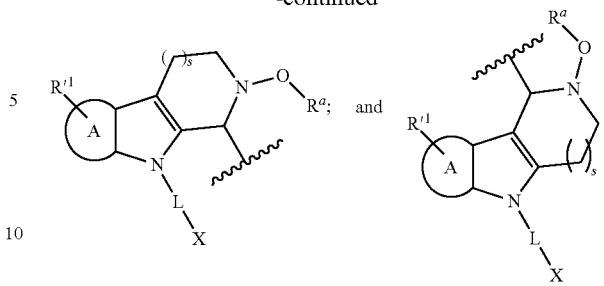

The following examples illustrate embodiments of the invention and are not intended to limit the scope of the compositions of the invention or the methods in which they find use.

EXAMPLES

Example 1

Materials and Methods

A. General Synthetic Methods

All reagents were obtained from Sigma-Aldrich, Acros, or TCI and used without further purification. Anhydrous solvents were dried and deoxygenated by purification through columns of alumina and Q-5 (1), with the exception of N,N-dimethylformamide, which was purchased in a sealed bottle and stored over molecular sieves. Deuterated solvents were purchased from Cambridge Isotope Laboratories. Solvents were removed on a Buchi Rotavapor R-114 equipped with a Welch 2026 self-cleaning dry vacuum pump or with an Edwards RV3 vacuum pump.

Thin layer chromatography was performed with Silicycle 60 Å silica gel plates and analyzed by UV illumination or $I_2$ staining. Flash chromatography was performed with Silicycle 60 Å 230-400 mesh silica gel. High-pressure liquid chomatography was performed on a Varian ProStar instrument with a UV absorption detector operating at 210 and 254 nm. Preparative-scale HPLC was performed on a 100 Å C18 reverse phase column (250×21.4 mm) with a solvent flow rate of 20 mL/min, or a Varian Microsorb 300-5 C4 reverse phase column (250×4.6 mm) with a solvent flow rate of 1 mL/min.

NMR spectra were acquired on Bruker AVQ-400, AVB-400, DRX-500, AV-500, or AV-600 spectrometers. $^1$H NMR spectra were referenced to residual CHCl$_3$ (7.26 ppm), CD$_2$HCN (1.94 ppm), or CD$_2$HOD (3.31 ppm). $^{13}$C NMR spectra were referenced to CDCl$_3$ (77.16 ppm), CD$_3$CN (1.32 ppm), or CD$_3$OD (49.00 ppm). NMR spectra were processed using MestReNova (Mestrelab Research S.L.). High-resolution ESI mass spectra of small molecules were obtained at the UC Berkeley Mass Spectrometery Facility on a Thermo LTQ Orbitrap mass spectrometer.

B. Synthesis of New Compounds

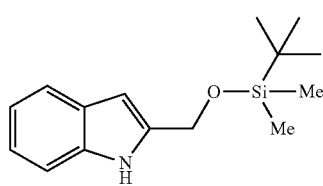 [SMILES: CC(C)(C)[Si](C)(C)OCc1cc2ccccc2[nH]1]

2-(((Tert-butyldimethylsilyl)oxy)methyl)-1H-indole (6)

An oven-dried flask was charged with indole-2-methanol (1.581 g, 10.74 mmol), TBSCl (1789 g, 11.87 mmol, 1.10 equiv), and imidazole (2.197 g, 32.27 mmol, 3.00 equiv), and this mixture was suspended in CH$_2$Cl$_2$ (40 mL, anhydrous). After 16 h, the reaction mixture was concentrated to an orange residue. The crude mixture was taken up in Et$_2$O (50 mL), washed with aqueous AcOH (5% v/v, 3×50 mL) and brine (25 mL). The combined organic layers were dried over sodium sulfate and concentrated to a crystalline solid (2.789 g, 10.67 mmol, 99%) which was used without further purification. R$_f$=0.5 in 9:1 hexanes:EtOAc. $^1$H NMR (500 MHz, CDCl$_3$) δ 8.29 (s, 1H), 7.57 (d, J=7.7 Hz, 1H), 7.37 (dd, J=8.1, 0.6 Hz, 1H), 7.19-7.14 (m, 1H), 7.12-7.07 (m, 1H), 6.32 (d, J=1.0 Hz, 1H), 4.89 (s, 2H), 0.95 (s, 9H), 0.12 (s, 6H). $^{13}$C NMR (101 MHz, CDCl$_3$) δ 138.3, 136.0, 128.6, 121.7, 120.5, 119.8, 110.9, 99.0, 59.4, 26.1, 18.5, −5.2. HRMS (ESI) calcd for C$_{15}$H$_{24}$NOSi [M+H]$^+$: 262.1627; found: 262.1625.

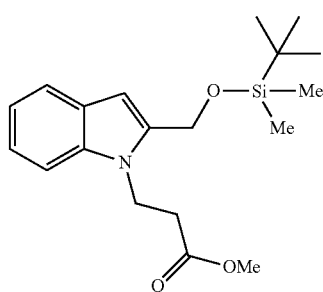 [SMILES: COC(=O)CCn1c(CO[Si](C)(C)C(C)(C)C)cc2ccccc21]

Methyl 3-(2-(((tert-butyldimethylsilyloxy)methyl)-1H-indol-1-yl)propanoate (7)

To a solution of 6 (2.789 g, 10.67 mmol) in acetonitrile (25 mL) was added methyl acrylate (4.80 mL, 53.3 mmol, 5.00 equiv) followed by 1,8-diazabicyclo[5.4.0]undec-7-ene (DBU; 800 µL, 5.35 mmol, 0.50 equiv), and the resulting mixture was brought to reflux. After 18 h, the solution was cooled and concentrated to an orange oil which was purified by silica gel chromatography (9:1 hexanes:EtOAc, R$_f$=0.4) to yield a colorless oil (3.543 g, 10.19 mmol, 96%). $^1$H NMR (400 MHz, CDCl$_3$) δ 7.58 (d, J=7.8 Hz, 1H), 7.34 (d, J=8.2 Hz, 1H), 7.23-7.18 (m, 1H), 7.12-7.07 (m, 1H), 6.38 (s, 1H), 4.84 (s, 2H), 4.54-4.49 (m, 2H), 2.89-2.84 (m, 2H), 0.91 (s, 9H), 0.10 (s, 6H). $^{13}$C NMR (101 MHz, CDCl$_3$) δ 172.0, 138.5, 137.1, 127.7, 122.0, 121.0, 119.8, 109.3, 101.8, 58.2, 51.9, 39.5, 34.6, 26.0, 18.4,-5.2. HRMS (ESI) calcd for C$_{19}$H$_{30}$NO$_3$Si [M+H]$^+$: 348.1995; found: 348.1996.

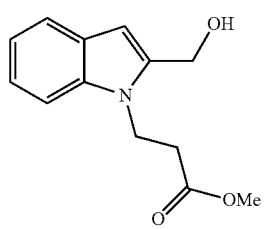 [SMILES: COC(=O)CCn1c(CO)cc2ccccc21]

Methyl 3-(2-(hydroxymethyl)-1H-indol-1-yl)propanoate (2)

To a solution of 7 (1.283 g, 3.692 mmol) in tetrahydrofuran (20 mL) at 0° C. was added tetrabutylammonium fluoride (1.0 M in THF, 3.90 mL, 3.90 mmol, 1.06 equiv). After 15 minutes, the reaction mixture was diluted with diethyl ether (20 mL) and washed with NaHCO$_3$ (sat. aq., 3×20 mL), and concentrated to a pale green oil. The oil was purified by silica gel chromatography (2:1 hexanes:EtOAc, R$_f$=0.25) to yield a white crystalline solid (822 mg, 3.524 mmol, 95%). $^1$H NMR (500 MHz, CDCl$_3$) δ 7.60 (d, J=7.8 Hz, 1H), 7.34 (dd, J=8.2, 0.4 Hz, 1H), 7.27-7.23 (m, 1H), 7.16-7.11 (m, 1H), 6.44 (s, 1H), 4.77 (s, 2H), 4.49 (t, J=7.3 Hz, 2H), 3.66 (s, 3H), 2.87 (t, J=7.3 Hz, 2H), 2.64 (s, 1H). $^{13}$C NMR (126 MHz, CDCl$_3$) δ 172.3, 138.5, 137.0, 127.6, 122.2, 121.1, 119.9, 109.3, 102.3, 57.1, 52.0, 39.1, 34.3. HRMS (ESI) calcd for C$_{13}$H$_{15}$NNaO$_3$ [M+Na]$^+$: 256.0950; found: 256.0946.

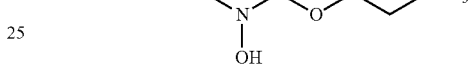

2-(Trimethylsilyl)ethyl hydroxy(methyl)carbamate (8)

To N-methylhydroxylamine hydrochloride (249 mg, 2.98 mmol, 1.05 equiv) was added KOH (0.1 M solution in MeOH, 30.0 mL, 3.00 mmol, 1.06 equiv), resulting in the formation of a white precipitate. After 5 minutes, N-[2-(trimethylsilyl)ethoxycarbonyloxy]succinimide (736 mg, 2.84 mmol) was added. After 4 h, the solution was concentrated and the residue was suspended in ethyl acetate (30 mL). The organic solution was washed with sodium bicarbonate (saturated aqueous solution, 3×15 mL) and brine (15 mL), dried over Na$_2$SO$_4$, and then concentrated to a colorless oil which was of sufficient purity for further use (466 mg, 2.44 mmol, 86%). R$_f$=0.2 in 4:1 hexanes:EtOAc. $^1$H NMR (500 MHz, CDCl$_3$) δ 7.35 (br s, 1H), 4.24-4.19 (m, 2H), 3.20 (s, 3H), 1.04-0.98 (m, 2H), 0.04 (s, 9H). $^{13}$C NMR (101 MHz, CDCl$_3$) δ 158.6, 65.0, 38.0, 17.9,-1.4. HRMS (ESI) calcd for C$_7$H$_{17}$NNaO$_3$Si [M+Na]$^+$: 214.0875; found: 214.0870.

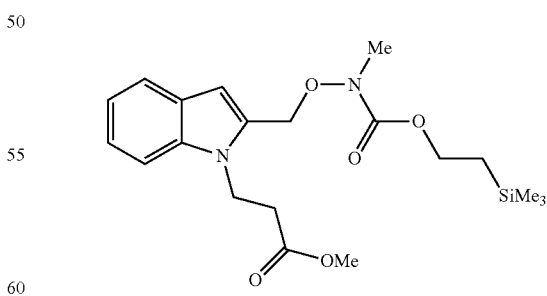

N-Methyl3-(2-(3,8,8-trimethyl-4-oxo-2,5-dioxa-3-aza-8-silanonyl)-1H-indol-1-yl)propanoate(9)

To an oven-dried flask charged with 2 (195 mg, 0.836 mmol), TeocN(Me)OH (201 mg, 1.05 mmol, 1.26 equiv), and tributylphosphine (251 µL, 1.05 mmol, 1.26 equiv) was added toluene (24 mL, anhydrous) followed by 1,1'-(azodicarbonyl)dipiperidine (263 mg, 1.04 mmol, 1.25 equiv). A thick, white precipitate formed over the course of the next hour, after which diethyl ether (40 mL) was added and the solution was filtered through Celite. The residue was concentrated to a yellow oil and then purified by silica gel chromatography (4:1 hexanes:EtOAc, $R_f$=0.3) to yield a colorless oil (299 mg, 736 µmol, 88%). $^1$H NMR (600 MHz, CDCl$_3$) δ 7.60 (d, J=7.9 Hz, 1H), 7.36 (d, J=8.2 Hz, 1H), 7.28-7.22 (m, 1H), 7.14-7.09 (m, 1H), 6.57 (s, 1H), 5.05 (s, 2H), 4.63 (t, J=7.4 Hz, 2H), 4.25-4.19 (m, 2H), 3.67 (s, 3H), 3.09 (s, 3H), 2.88 (t, J=7.4 Hz, 2H), 1.02-0.96 (m, 2H), 0.05 (s, 9H). $^{13}$C NMR (151 MHz, CDCl$_3$) δ 171.9, 158.0, 137.3, 133.3, 127.5, 122.8, 121.4, 120.0, 109.6, 105.4, 68.0, 64.8, 51.9, 39.3, 37.0, 34.7, 17.9, -1.4. HRMS (ESI) calcd for C$_{20}$H$_{30}$N$_2$NaO$_5$Si [M+Na]$^+$: 429.1822; found: 429.1816.

3-(2-(((Methylamino)oxy)methyl)-1H-indol-1-yl)propanoic acid (1a)

To a mixture of 3 (107 mg, 273 µmol) and CsF (241 mg, 1.59 mmol, 5.81 equiv) was added N,N-dimethylformamide (5 mL, anhydrous). After 20 h, H$_2$O (3 mL) was added, resulting in evolution of a gas. The solution was concentrated and purified by silica gel chromatography (5% AcOH, 3% MeOH in CH$_2$Cl$_2$, $R_f$=0.45), affording a white solid (69 mg, 274 µmol, 100%). $^1$H NMR (500 MHz, CD$_3$OD) δ 7.51 (d, J=7.9 Hz, 1H), 7.40 (d, J=8.3 Hz, 1H), 7.19-7.14 (m, 1H), 7.05-7.00 (m, 1H), 6.47 (s, 1H), 4.89 (s, 2H), 4.54-4.50 (m, 2H), 2.83-2.75 (m, 2H), 2.66 (s, 3H). $^{13}$C NMR (151 MHz, CD$_3$OD) δ 175.1, 138.5, 136.2, 129.0, 123.1, 121.8, 120.6, 110.4, 104.7, 68.0, 40.4, 38.9, 35.6. HRMS (ESI) calcd for C$_{13}$H$_{17}$N$_2$O$_3$ [M+H]$^+$: 249.1239; found: 249.1232.

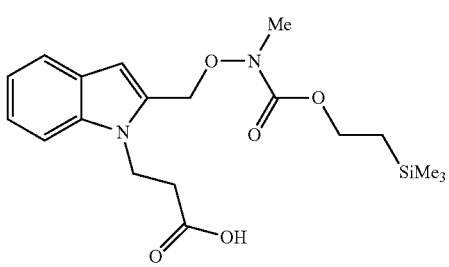 [SMILES: CN(OCc1cc2ccccc2n1CCC(=O)O)C(=O)OCC[Si](C)(C)C]

3-(2-(3,8,8-Trimethyl-4-oxo-2,5-dioxa-3-aza-8-silanonyl)-1H-indol-1-yl)propanoic acid (3)

To a solution of 9 (366 mg, 900 µmol in dioxane (7 mL) was added LiOH (0.5 M aqueous solution, 3.60 mL, 1.80 mmol, 2.00 equiv). After 2 h, the reaction was quenched with AcOH (5% v/v aqueous solution, 10 mL) to pH 4, resulting in the formation of a white precipitate. The solution was extracted with EtOAc (3×10 mL). The organic extract was concentrated to a yellow oil and purified by silica gel chromatography (2:1 hexanes:EtOAc with 2% AcOH, $R_f$=0.4), yielding a tan solid (292 mg, 744 µmol, 83%). $^1$H NMR (600 MHz, CDCl$_3$) δ 10.95 (br s, 1H), 7.61 (d, J=7.9 Hz, 1H), 7.38 (d, J=8.3 Hz, 1H), 7.28-7.23 (m, 1H), 7.15-7.10 (m, 1H), 6.58 (s, 1H), 5.04 (s, 2H), 4.67-4.59 (m, 2H), 4.25-4.19 (m, 2H), 3.11 (s, 3H), 2.98-2.90 (m, 2H), 1.04-0.94 (m, 2H), 0.04 (s, 9H). $^{13}$C NMR (151 MHz, CDCl$_3$) δ 176.4, 158.0, 137.2, 133.1, 127.5, 122.9, 121.5, 120.2, 109.5, 105.5, 68.0, 65.0, 39.1, 37.0, 34.8, 17.9,-1.4. HRMS (ESI) calcd for C$_{19}$H$_{28}$N$_2$NaO$_5$Si [M+Na]$^+$: 415.1665; found: 415.1666.

3-(1-Isopropyl-2-methyl-1,2-dihydro-11,21oxazino[5,4-b]indol-5(4H)-yl)propanoic acid (10)

To a solution of 1a (6.0 mg, 24 µmol) in 1:1 aqueous NH$_4$OAc (20 mM, pH 4.50):MeOH (2 mL) was added isobutyraldehyde (6.6 µL, 72 µmol, 3 equiv). After 1 h, the reaction mixture was concentrated to a pale pink solid (7.0 mg, 23 µmol, 96%). $R_f$=0.4 in 5% AcOH, 3% MeOH in CH$_2$Cl$_2$. $^1$H NMR (600 MHz, CDCl$_3$) δ 7.49 (d, J=7.9 Hz, 1H), 7.32 (d, J=8.1 Hz, 1H), 7.20-7.15 (m, 1H), 7.12-7.07 (m, 1H), 5.00 (d, J=14.8 Hz, 1H), 4.78 (d, J=14.9 Hz, 1H), 4.32-4.18 (m, 2H), 3.55 (d, J=5.7 Hz, 1H), 2.76 (t, J=6.8 Hz, 2H), 2.67 (s, 3H), 2.27-2.18 (m, 1H), 1.08 (d, J=6.8 Hz, 3H), 1.02 (d, J=6.8 Hz, 3H). $^{13}$C NMR (151 MHz, CDCl$_3$) δ 175.2, 136.2, 130.4, 127.8, 121.5, 119.6, 119.6, 109.2, 107.0, 66.8, 58.3, 41.6, 39.3, 34.5, 33.2, 20.6, 20.6. HRMS (ESI) calcd for C$_{17}$H$_{23}$N$_2$O$_3$ [M+H]$^+$: 303.1709; found: 303.1701.

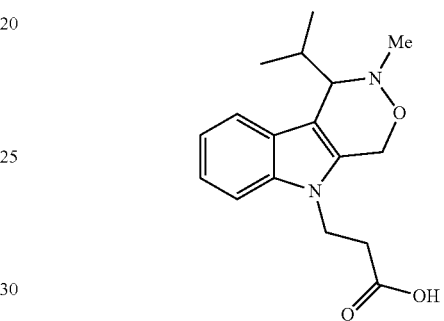

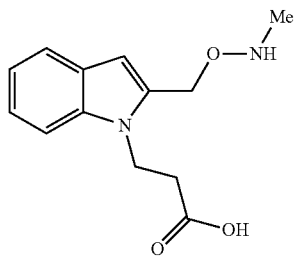 [SMILES: CNOCc1cc2ccccc2n1CCC(=O)O]

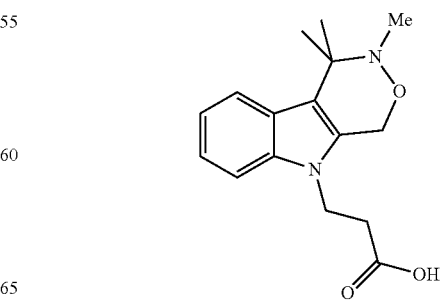

3-(1,1,2-Trimethyl-1,2-dihydro-[1,2]oxazino[5,4-b]indol-5(4H)-yl)propanoic acid (11)

To a solution of 1a (5.8 mg, 23 µmol) in 1:1 aqueous NH$_4$OAc (20 mM, pH 4.50):MeOH (2 mL) was added acetone (5.1 µL, 69 µmol, 3 equiv). After 1 h, the reaction mixture was concentrated to a colorless oil (6.8 mg, 24 µmol, 100%). R$_f$=0.5 in 5% AcOH, 3% MeOH in CH$_2$Cl$_2$. $^1$H NMR (600 MHz, CD$_3$CN) δ 7.60 (d, J=7.9 Hz, 1H), 7.39 (d, J=8.2 Hz, 1H), 7.15-7.10 (m, 1H), 7.07-7.03 (m, 1H), 4.92 (br s, 2H), 4.22 (t, J=6.7 Hz, 2H), 2.70 (t, J=6.8 Hz, 2H), 2.66 (s, 3H), 1.45 (s, 6H). $^{13}$C NMR (151 MHz, CD$_3$CN) δ 173.0, 137.2, 134.1, 125.7, 121.4, 120.0, 119.8, 116.9, 110.6, 65.8, 60.0, 40.0, 37.1, 34.69, 34.66. HRMS (ESI) calcd for C$_{16}$H$_{21}$N$_2$O$_3$ [M+H]$^+$: 289.1552; found: 289.1544.

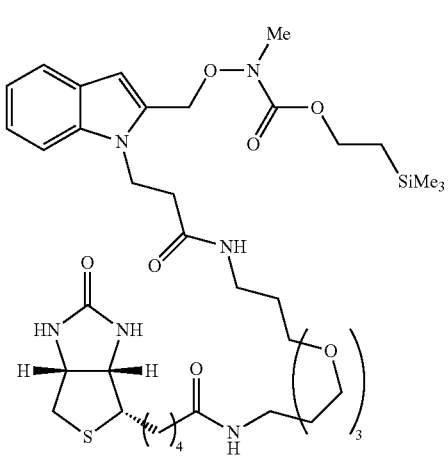

2-(Trimethylsilyl)ethyl methyl((1-(3-oxo-3-((3-(3-(2-((3aS,4S,6aR)-2-oxohexahydro-1H-thieno[3,4-d]imidazol-4-yl)acetamido)propoxy)propyl)amino)propyl)-1H-indol-2-yl)methoxy)carbamate (12)

To an oven-dried flask charged with 3 (6.5 mg, 17 µmol) and diisopropylethylamine (9.0 µL, 51 µmol, 3.0 equiv) in CH$_2$C$_{12}$ (1 mL, anhydrous) at 0° C. was added pentafluorophenyl trifluoroacetate (3.0 µL, 17 µmol, 1.0 equiv). The solution was allowed to warm to room temperature over the next 30 min, after which it was filtered through a 0.5 cm$^3$ silica plug which was washed with CH$_2$C$_{12}$ (2 mL). The filtrate was concentrated and dissolved in N,N-dimethylformamide (3×0.5 mL, anhydrous), then added to a solution of biotin-PEG$_3$-NH$_2$ (7.7 mg, 17 µmol, 1.0 equiv) and diisopropylethylamine (9.0 µl, 51 µmol, 3.0 equiv) in N,N-dimethylformamide (0.5 mL, anhydrous). After 24 h, the solution was concentrated and then purified by silica gel chromatography (8% MeOH in CH$_2$C$_{12}$, R$_f$=0.1), affording a white solid (10.2 mg, 12.4 µmol, 75%). $^1$H NMR (500 MHz, CDCl$_3$) δ 7.56 (d, J=7.9 Hz, 1H), 7.43 (d, J=8.2 Hz, 1H), 7.24-7.19 (m, 1H), 7.10-7.05 (m, 1H), 6.82 (s, 1H), 6.59-6.54 (m, 2H), 6.00 (s, 1H), 5.19 (s, 1H), 5.03 (s, 2H), 4.60 (t, J=7.3 Hz, 2H), 4.46-4.41 (m, 1H), 4.26-4.22 (m, 1H), 4.20 (dd, J=9.5, 7.7 Hz, 2H), 3.58-3.49 (m, 8H), 3.45 (m, 2H), 3.34 (t, J=6.1 Hz, 2H), 3.30 (dd, J=12.1, 6.0 Hz, 2H), 3.23 (q, J=6.5 Hz, 2H), 3.13 (s, 3H), 3.12-3.07 (m, 1H), 2.86 (dd, J=12.8, 5.0 Hz, 1H), 2.72 (t, J=7.3 Hz, 2H), 2.68 (d, J=12.9 Hz, 1H), 2.16 (t, J=7.4 Hz, 2H), 1.74-1.70 (m, 2H), 1.67-1.60 (m, 6H), 1.45-1.37 (m, 2H), 1.03-0.95 (m, 2H), 0.04 (s, 9H). $^{13}$C NMR (126 MHz, CDCl$_3$) δ 173.1, 170.8, 163.6, 157.8, 137.4, 133.1, 127.3, 122.7, 121.1, 119.9, 110.1, 105.3, 70.52, 70.45, 70.2, 70.1, 69.9, 69.2, 67.7, 64.9, 61.9, 60.2, 55.6, 40.64, 40.57, 38.0, 37.7, 37.3, 36.9, 36.0, 29.8, 29.0, 28.2, 28.2, 25.7, 17.9, −1.4. HRMS (ESI) calcd for C$_{39}$H$_{64}$N$_6$NaO$_9$SSi [M+Na]$^+$: 843.4122; found: 843.4125.

3-(2-(((Methylamino)oxy)methyl)-1H-indol-1-yl)-N-(3-(3-(2-((3aS,4S,6aR)-2-oxohexahydro-1H-thieno[3,4-d]imidazol-4-yl)acetamido)propoxy)propyl)propanamide (1b)

To an oven-dried flask charged with 12(2.2 mg, 2.7 µmol) and CsF (6.5 mg, 43 µmol, 16 equiv) was added N,N-dimethylformamide (0.5 mL, anhydrous). After 2 h, H$_2$O (1 mL) and MeOH (1 mL) were added and the reaction mixture was concentrated to a white residue. The crude product was purified by silica gel chromatography (65:20:20:2.5:2.5 EtOAc:MeCN:MeOH:H$_2$O:NH$_4$OH, R$_f$=0.25), yielding a colorless oil (1.8 mg, 2.7 µmol, 99%). $^1$H NMR (500 MHz, CDCl$_3$) δ 7.55 (d, J=7.9 Hz, 1H), 7.40 (d, J=8.2 Hz, 1H), 7.21-7.17 (m, 1H), 7.10-7.04 (m, 1H), 6.65 (br s, 1H), 6.50 (s, 1H), 6.49 (br s, 1H), 5.71 (br s, 1H), 4.88 (s, 2H), 4.83 (br s, 1H), 4.55 (t, J=7.1 Hz, 2H), 4.42-4.37 (m, 1H), 4.24-4.19 (m, 1H), 3.58-3.48 (m, 8H), 3.47-3.43 (m, 2H), 3.36 (t, J=5.9 Hz, 2H), 3.32-3.28 (m, 2H), 3.26-3.21 (m, 2H), 2.85 (dd, J=12.8, 5.0 Hz, 1H), 2.67 (t, J=7.1 Hz, 2H), 2.62 (d, J=12.8 Hz, 1H), 2.15 (t, J=7.3 Hz, 2H), 1.72-1.69 (m, 2H), 1.68-1.59 (m, 6H), 1.44-1.38 (m, 2H). $^{13}$C NMR (126 MHz, CDCl$_3$) δ 173.0, 170.9, 163.4, 137.3, 135.5, 127.6, 122.2, 121.0, 119.8, 110.0, 103.7, 70.5, 70.4, 70.0, 69.8, 69.4, 67.3, 61.9, 60.1, 55.6, 40.7, 40.3, 39.4, 38.2, 37.5, 37.3, 36.0, 29.9, 28.9, 28.7, 28.2, 28.1, 25.7. HRMS (ESI) calcd for $C_{33}H_{53}N_6O_7S$ [M+H]$^+$: 677.3696; found: 677.3691.

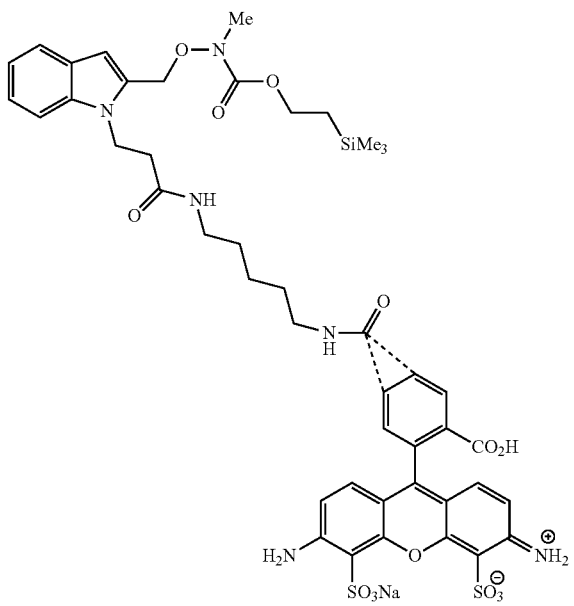

Sodium 6-amino-9-(2-carboxy-4-((5-(3-(2-(3,8,8-trimethyl-4-oxo-2,5-dioxa-3-aza-8-silanonyl)-1H-indol-1-yl)propanamido)pentyl)carbamoyl)phenyl)-3-iminio-3H-xanthene-4,5-disulfonate and sodium 6-amino-9-(2-carboxy-5-((5-(3-(2-(3,8,8-trimethyl-4-oxo-2,5-dioxa-3-aza-8-silanonyl)-1H-indol-1-yl)propanamido)pentyl)carbamoyl)phenyl)-3-iminio-3H-xanthene-4,5-disulfonate (13)

To an oven-dried flask charged with 3 (9.8 mg, 25 µmol) and diisopropylethylamine (13 µL, 75 µmol, 3.0 equiv) in CH$_2$Cl$_2$ (1 mL, anhydrous) at 0° C. was added pentafluorophenyl trifluoroacetate (4.5 µl, 26 µmol, 1.0 equiv). The solution was allowed to warm to room temperature over the next 45 min, after which it was filtered through a 0.5 cm$^3$ silica plug which was washed with CH$_2$Cl$_2$ (2 mL). The filtrate was concentrated and dissolved in N,N-dimethylformamide (2.0 mL, anhydrous). To 200 µl of this solution was added diisopropylethylamine (4.5 µL, 26 µmol, 17 equiv) and a solution of AF488 cadaverine (1.0 mg, 1.6 µmol) in N,N-dimethylformamide (1.0 mL, anhydrous). After 21 h, MeOH (1 mL) was added and the reaction mixture was concentrated to a red residue which was purified by HPLC on a C18 column (time (min), % acetonitrile in H$_2$O: 0, 10; 5, 10; 35, 100). The product was isolated as a red powder (1.17 mg, 1.15 µmol, 74%). HRMS (ESI) calcd for $C_{45}H_{51}N_6Na_2O_{14}S_2Si$ [M+Na]+: 1037.2469; found: 1037.2488.

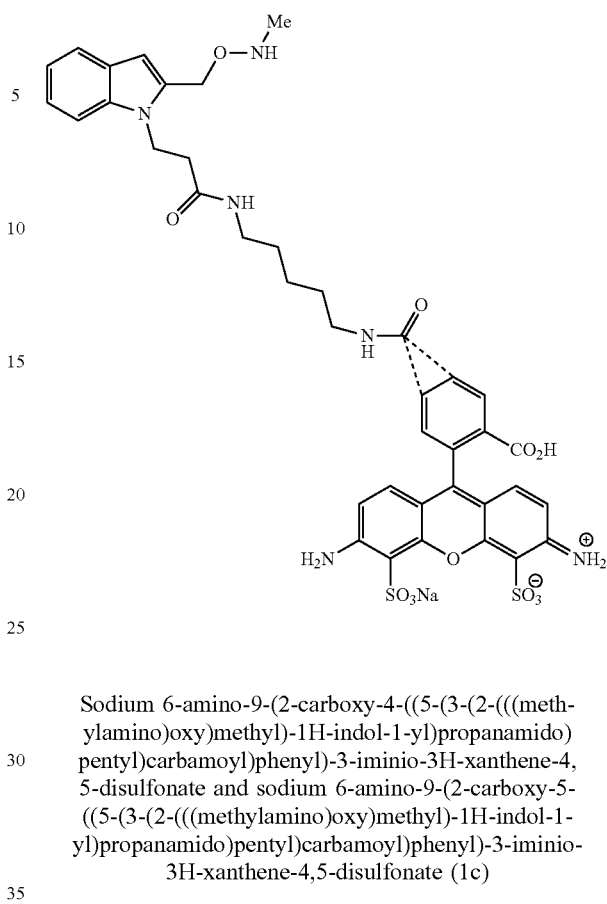

Sodium 6-amino-9-(2-carboxy-4-((5-(3-(2-(((methylamino)oxy)methyl)-1H-indol-1-yl)propanamido)pentyl)carbamoyl)phenyl)-3-iminio-3H-xanthene-4,5-disulfonate and sodium 6-amino-9-(2-carboxy-5-((5-(3-(2-(((methylamino)oxy)methyl)-1H-indol-1-yl)propanamido)pentyl)carbamoyl)phenyl)-3-iminio-3H-xanthene-4,5-disulfonate (1c)

To an oven-dried flask charged with 13 (1.166 mg, 1.149 µmol) and CsF (31 mg, 204 µmol, 178 equiv) was added N,N-dimethylformamide (anhydrous, 0.5 mL). After 6 h, H$_2$O (1 mL) was added and the reaction mixture was concentrated to a dark red residue which was purified by HPLC on a C4 column (time (min), % acetonitrile in H$_2$O: 0, 5; 5, 5; 10, 10). The resulting product was dissolved in 9:1 MeCN:H$_2$O (3×0.5 mL) and filtered to remove residual CsF, resulting in a red solid (871 µg, 1.00 µmol, 87%). R$_f$=0.20 in 6:2:2:2 EtOAc:MeOH:MeCN:H$_2$O. in HRMS (ESI) calcd for $C_{39}H_{39}N_6O_{12}S_2$ [M−Na]$^-$: 847.2067; found: 847.2078.

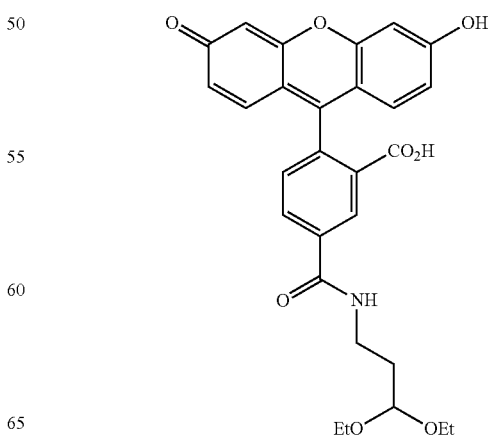

5-((3,3-Diethoxypropyl)carbamoyl)-2-(6-hydroxy-3-oxo-3H-xanthen-9-yl)benzoic acid (14)

To a mixture of 5-carboxyfluorescein (30 mg, 80 μmol), N-(3-dimethylaminopropyl)-N'-ethylcarbodiimide hydrochloride (31 mg, 162 μmol, 2.0 equiv), and 1-hydroxybenzotriazole hydrate (20 wt % $H_2O$, 55 mg, 326 μmol) was added N,N-dimethylformamide (3 mL) followed by triethylamine (22.2 μL, 159 μmol, 2.0 equiv) and 3-aminopropionaldehyde diethyl acetal (13 μL, 80 μmol, 1.0 equiv). After being stirred in the dark for 26 h, MeOH (1 mL) was added and the solution was concentrated to an orange oil which was purified by silica gel chromatography (8% MeOH in $CH_2Cl_2$, $R_f$=0.35) and HPLC on a C18 column (time (min), % MeCN in $H_2O$ with 0.1% TFA: (0, 45; 3, 45; 15, 55). The product was obtained as a bright orange powder (13 mg, 26 μmol, 32%). $^1$H NMR (500 MHz, $CD_3OD$) δ 8.41 (d, J=0.9 Hz, 1H), 8.17 (dd, J=8.0, 1.5 Hz, 1H), 7.30 (d, J=8.0 Hz, 1H), 6.68 (d, J=2.3 Hz, 2H), 6.61 (d, J=8.7 Hz, 2H), 6.53 (dd, J=8.7, 2.3 Hz, 2H), 4.65 (t, J=5.5 Hz, 1H), 3.75-3.67 (m, 2H), 3.59-3.53 (m, 2H), 3.51 (t, J=7.1 Hz, 2H), 1.95 (dt, J=8.6, 4.3 Hz, 2H), 1.20 (t, J=7.1 Hz, 6H). $^{13}$C NMR (151 MHz, $CD_3OD$) δ 170.7, 168.3, 162.4, 155.5, 154.4, 137.9, 135.0, 130.3, 129.5, 126.1, 125.0, 114.2, 111.2, 103.7, 103.0, 98.2, 63.0, 37.3, 34.5, 15.7. HRMS (ESI) calcd for $C_{28}H_{28}NO_8$ [M+H]$^+$: 506.1815; found: 506.1823.

The product was purified by silica gel chromatography (10% MeOH in $CH_2Cl_2$, $R_f$=0.2), resulting in an orange solid (8.8 mg, 20 μmol, 79%; 97% brsm). $^1$H NMR (500 MHz, $CDCl_3$) δ 8.46 (s, 1H), 8.20 (d, J=8.0 Hz, 1H), 7.34 (d, J=8.0 Hz, 1H), 6.81-6.58 (m, 6H), 4.67 (t, J=5.4 Hz, 1H), 3.53 (t, J=7.0 Hz, 2H), 1.93 (dt, J=14.2, 7.1 Hz, 2H). HRMS (ESI) calcd for $C_{24}H_{16}NO_7$ [M–H]$^-$: 430.0927; found: 430.0917.

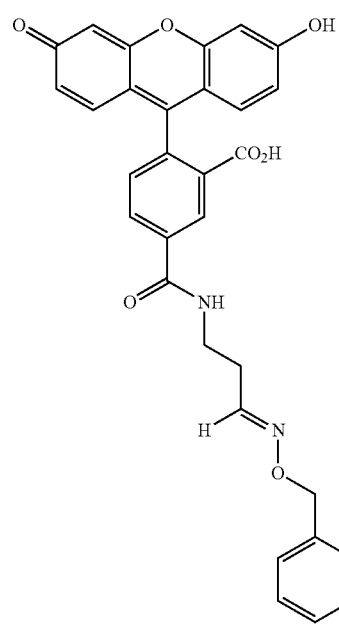

5-((3-((Benzyloxy)imino)propyl)carbamoyl)-2-(6-hydroxy-3-oxo-3H-xanthen-9-yl)benzoic acid (5a)

A mixture of 4 (3.2 mg, 7.4 μmol) and O-benzylhydroxylamine hydrochloride (1.3 mg, 8.1 μmol, 1.1 equiv) was dissolved in 1:1 aqueous sodium acetate (100 mM, pH 4.50):MeOH (1 mL). After 2.5 h, the resulting suspension was concentrated to an orange solid that was purified by HPLC on a C18 column (time (min), % MeCN in $H_2O$: 0, 40; 5, 40; 15, 55), affording an orange solid (3.2 mg, 6.0 μmol, 81%). The product was isolated as a mixture of syn:anti isomers in a 9:11 ratio. $^1$H NMR (500 MHz, $CD_3OD$) δ 8.40 (d, J=4.0 Hz, 1H), 8.16-8.08 (m, 1H), 7.54 (t, J=5.9 Hz, 0.6H, anti-C(H)NO), 7.32-7.15 (m, 6H), 6.87 (t, J=5.5 Hz, 0.4H, syn-C(H)NO), 6.69 (t, J=2.2 Hz, 2H), 6.68-6.62 (m, 2H), 6.56 (t, J=2.3 Hz, 1H), 6.54 (t, J=2.4 Hz, 1H), 5.08 (s, syn-$CH_2O$, 0.9H), 5.01 (s, anti-$CH_2O$, 1.1H), 3.61 (t, J=6.6 Hz, 2H), 2.75 (q, J=6.3 Hz, syn-$CH_2C(H)N$, 0.9H), 2.53 (q, J=6.4 Hz, anti-$CH_2C(H)N$, 1.1H). HRMS (ESI) calcd for $C_{31}H_{25}N_2O_7$ [M+1–1]$^+$: 537.1662; found: 537.1670.

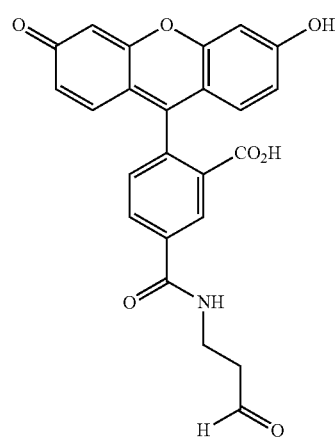 [SMILES: O=CCCNC(=O)c1ccc(-c2c3ccc(=O)cc-3oc3cc(O)ccc23)c(C(=O)O)c1]

2-(6-Hydroxy-3-oxo-3H-xanthen-9-yl)-5-((3-oxopropyl)carbamoyl)benzoic acid (Shen B-Q. et al. (2012), "Conjugation site modulates the in vivo stability and therapeutic activity of antibody-drug conjugates," *Nat. Biotechnol.* 30(2):184-189): Compound 14 (13 mg, 26 μmol) was dissolved in 12:12:1 $CH_2Cl_2$:trifluoroacetic acid:$H_2O$ (1 mL) and heated to 42° C. in a sealed vial. After 18 h, the reaction was quenched with $H_2O$ (2 mL) and the solution was concentrated to an orange oil.

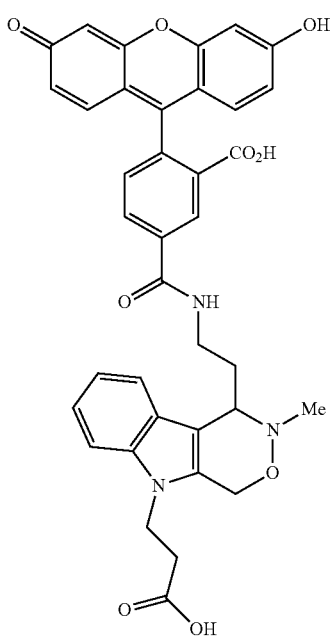 [SMILES: CN1OCc2c(c3ccccc3n2CCC(=O)O)C1CCNC(=O)c1ccc(-c2c3ccc(=O)cc-3oc3cc(O)ccc23)c(C(=O)O)c1]

5-((2-(5-(2-Carboxyethyl)-2-methyl-1,2,4,5-tetrahydro-[1,2]oxazino [5,4-b]indol-1-yl)ethyl)carbamoyl)-2-(6-hydroxy-3-oxo-3H-xanthen-9-yl)benzoic acid (5b)

A mixture of 4 (3.2 mg, 7.4 μmol) and 1a (2.0 mg, 8.1 μmol, 1.1 equiv) was dissolved in 1:2 aqueous sodium acetate (100 mM, pH 4.50):MeOH (1.5 mL). After 2.5 h, the reaction mixture was concentrated to an orange solid that was purified by HPLC on a C18 column (time (min), % MeCN in H$_2$O: 0, 40; 5, 40; 15, 55), affording an orange solid (3.7 mg, 5.6 μmol, 76%). $^1$H NMR (500 MHz, CD$_3$OD) δ 8.07 (s, 1H), 7.85 (dd, J=8.0, 1.3 Hz, 1H), 7.51 (d, J=7.8 Hz, 1H), 7.35 (d, J=8.1 Hz, 1H), 7.17 (d, J=8.0 Hz, 1H), 7.08-7.03 (m, 1H), 7.03-6.98 (m, 1H), 6.68 (d, J=1.9 Hz, 2H), 6.62-6.52 (m, 4H), 5.12 (d, J=14.4 Hz, 1H), 5.05 (d, J=14.5 Hz, 1H), 4.37-4.27 (m, 2H), 4.11 (br s, 1H), 3.59 (dt, J=13.2, 6.4 Hz, 1H), 3.50 (dt, J=13.7, 6.9 Hz, 1H), 2.88 (s, 3H), 2.75-2.63 (m, 2H), 2.52 (m, 1H), 2.29 (m, 1H). HRMS (ESI) calcd for C$_{37}$H$_{32}$N$_3$O$_9$ [M+H]$^+$: 662.2138; found: 662.2154.

C. Small Molecule Experiments $^1$H NMR kinetics: Deuterated sodium acetate buffers were prepared by basifying solutions of acetic acid-d$_4$ in D$_2$O to the appropriate pD (pD=pH meter reading+0.41) (2) by addition of NaOD in D$_2$O and diluting them to 100 mM [acetate-d$_3$] with D$_2$O. Deuterated sodium phosphate buffers were prepared by combining 100 mM solutions of phosphoric acid-d$_3$ in D$_2$O and Na$_3$PO$_4$ in D$_2$O to the appropriate pD. For determination of the order of each reactant in the rate equation, stock solutions containing 1a (1.5 mM or 3.0 mM) or isobutyraldehyde (1.5 mM or 3.0 mM) in deuterated buffer solution were combined in a 1:1 ratio immediately before NMR acquisition. For determination of rate constants, stock solutions containing 1a (1 mM) or isobutyraldehyde (1 mM) in deuterated buffer solution were combined in a 1:1 ratio immediately before NMR acquisition (stock solutions containing 1.5 mM of each reactant were used at pD 7.0). All kinetic data were acquired on a Bruker AV-500 or AV-600 spectrometer with the probe temperature maintained at 295 K. 8-spectrum scan sets were acquired every 30 s, and all reactions were followed for at least one half-life. The disappearance of the N—CH$_2$ resonance was followed over time and the methyl resonances of the product were integrated to determine the total amount of material in solution. Data was analyzed in MestReNova and Microsoft Excel.

Small molecule hydrolysis: Hydrolysis solutions contained 1 μM 5a or 5b, 25 μM phenylalanine as an internal standard, and 5 mM sodium acetate at the appropriate pH. The solutions were incubated at room temperature and 50 μL aliquots were repeatedly analyzed by liquid chromatography on an Agilent 1200 instrument using an Agilent Poroshell 120 EC-C18 reverse phase column (4.6×50 mm) with a solvent flow rate of 0.4 mL/min. The following gradient was employed (time (min), % MeCN in H$_2$O with 0.1% TFA): 0, 5; 10, 95; 12, 95; 14, 5; 19, 5. The time of the first injection for each solution was assigned as t=0. Integrals of the absorption peaks for 5a and 5b at 440 nm were normalized against the phenylalanine peak for each injection.

D. Biotinylation of Glyoxal-Mb

Preparation of glyoxal-Mb: Transamination of horse heart myoglobin (Sigma-Aldrich) was performed following a modified literature protocol (3). Stock solutions of myoglobin (50 μM) in sodium phosphate buffer (25 mM, pH 6.50) and pyridoxal 5'-phosphate (PLP, 200 mM) in sodium phosphate buffer (25 mM, pH adjusted to 6.50) were prepared. The myoglobin solution was combined with an equal volume of the PLP stock solution or vehicle (25 mM sodium phosphate, pH 6.50) and incubated at 37° C. for 1 h in the dark. The solutions were then diluted 10-fold and exchanged into sodium phosphate buffer (25 mM, pH 6.50) 5 times using centrifugal concentrators (Amicon Ultra, 10 kDa MWCO), and then dialyzed against sodium phosphate buffer (10 mM, pH 6.50) to remove residual pyridoxal phosphate.

Time-dependent labeling: Glyoxal-Mb or Mb (3 μg) and 1b or N-(aminooxyacetyl)-N'-(D-biotinoyl)hydrazine(aminooxy-biotin) (250 μM) were combined in sodium acetate buffer (25 mM, pH 4.00) in a 4 μl reaction volume at 37° C. for 0-120 min and then quenched with benzaldehyde (10 mM).

Concentration-dependent labeling: Glyoxal-Mb or Mb (3 μg) and 1b or aminooxy-biotin (0-200 μM) were combined in sodium acetate buffer (100 mM, pH 4.00) in a 4 μL reaction volume at 37° C. for 3 h and then quenched with benzaldehyde (10 mM).

pH-dependent labeling: Glyoxal-Mb or Mb (1.7 μg) and 1b or aminooxy-biotin (250 μM) were combined in sodium acetate (100 mM, pH 4.00-5.50) or sodium phosphate (100 mM, pH 6.00-7.50) buffer in a 4 μL reaction volume at 37° C. for 3 h and then quenched with benzaldehyde (10 mM).

Co-treatment with BnONH$_2$: Glyoxal-Mb or Mb (1.7 μg), 1b (100 μM), and BnONH$_3$Cl (0-800 μM) were combined in sodium acetate buffer (100 mM, pH 4.50) in a 5 μL reaction volume at 37° C. for 3 h and then quenched with benzaldehyde (10 mM).

Co-treatment with aniline: Glyoxal-Mb or Mb (1.7 μg), 1b (100 μM), and anilinium acetate (0-50 mM, pH 4.50 or 5.50) or anilinium phosphate (0-50 mM, pH 6.50) buffer were combined in sodium acetate buffer (50 mM, pH 4.50 or 5.50) or sodium phosphate buffer (50 mM, pH 6.50) in a μL reaction volume at 37° C. for 4 h and then quenched with benzaldehyde (10 mM).

General procedure for Western blots: Reaction mixtures were incubated for 5 min at room temperature after addition of benzaldehyde, then combined with 33% (v/v) 4×SDS loading buffer with B-mercaptoethanol and run on a 26-well Bio-Rad Criterion XT 4-12% bis-tris gel (45 min, 175 V) in XT MES buffer. The contents of the gel were then wet-transferred to nitrocellulose membranes in tris-glycine buffer with 20% MeOH (60 min, 100 V) and total protein loading was imaged with Ponceau S stain (0.1% w/v in 5% v/v acetic acid). The blots were then blocked overnight at 4° C. in phosphate-buffered saline with 0.1% Tween-20 (PBST) containing bovine serum albumin (4% w/v). The blot in blocking solution was then incubated with mouse α-biotin FITC (Jackson ImmunoResearch, 1/10000) for 1h at room temperature, washed with PBST (3×10 min), and imaged. Western blots were scanned on an Amersham Typhoon 9410 imager and data were analyzed in ImageJ.

E. Preparation and Evaluation of FGly-MBP Conjugates

FGly-MBP and MBP C390A were prepared as previously described (Shen B-Q., et al. (2012), "Conjugation site modulates the in vivo stability and therapeutic activity of antibody-drug conjugates," *Nat. Biotechnol.* 30(2):184-189).

ESI-MS of full-length protein conjugates: Conjugation reactions of MBP with 1a for mass spectrometry analysis were prepared by combining FGly-MBP or MBP C390A (6.8 μg) with 1a (1 mM) in sodium acetate buffer (100 mM, pH 5.0) in a 8 μL reaction volume at 37° C. for 12 h. The reactions were then quenched by addition of dibasic sodium phosphate (100 mM, 92 μL) to bring the pH to 7.9, and stored at 4° C. for less than 1 h prior to analysis by ESI-MS.

Tryptic digest: A conjugate of FGly-MBP with 1a (5.7 μg) in sodium phosphate buffer (65 mM, pH 7.2) was incubated with dithiothreitol (DTT, 2.54 mM, 60 nmol) at 56° C. for 30 min, iodoacetamide (5.98 mM, 150 nmol) at room temperature for 1 h in the dark, and then DTT (2.33 mM, 60 nmol) at room temperature for 5 min (although no cysteine residues are present in FGly-MBP, DTT and iodoacetamide were added to show that the oxacarboline moiety is compatible with standard reduction and alkylation procedures employed in proteolytic digestion). The resulting sample was treated with trypsin (0.115 μg, 2 wt %) at 37° C. for 18 h. The solution was then acidified with formic acid to a final concentration of 1% and purified on Millipore ZipTip C18 resin, eluting with a solution of 70% MeCN and 1% formic acid in $H_2O$. The eluant was concentrated by centrifugal evaporation and the resulting residue was resuspended in water prior to analysis at the UC Berkeley HHMI Mass Spectrometry Lab by flow injection on a Bruker Apex-Qe ESI-Q-FT-ICR mass spectrometer (9.4T). HRMS (ESI) calcd for $C_{45}H_{70}N_{13}O_{15}$ $[M+H]^+$: 1032.5114; found: 1032.5220.

Thrombin cleavage: A solution of FGly-MBP (44 μg) was labeled with AF488 $C_5$-aminooxyacetamide or 1c (200 μM) in sodium acetate buffer (100 mM, pH 4.5) in a 20 μL reaction volume at 37° C. for 17 h. The solutions were diluted 10-fold and exchanged into PBS 5 times using a centrifugal concentrator (Amicon Ultra, 30 kDa MWCO). Solutions of the resulting AF488-MBP conjugates (0.6 μg) in PBS were incubated with thrombin (0-1.2 U) in a 6 μL reaction volume at 37° C. for 1 h and then quenched by addition of reducing SDS loading buffer and boiling for 5 min prior to resolution by SDS-PAGE. The gel was imaged and then stained with Colloidal blue (Life Technologies).

Fluorescence polarization: Oxime and oxacarboline-linked AF488-MBP conjugates were prepared as described above. Amide-linked AF488-MBP was prepared by treatment of FGly-MBP (44 μg) with AF488 5-SDP ester (500 μM) in sodium bicarbonate buffer (100 mM, pH 8.0) in a 15 μL reaction volume at 37° C. for 45 min. The solution was then diluted 10-fold and exchanged into PBS 5 times using a centrifugal concentrator (Amicon Ultra, 30 kDa MWCO). After evaluating conjugation efficiency by UV-vis, solutions of each conjugate containing 100 nM AF488 were prepared in PBS (100 μL) in triplicate. The solutions were incubated in a sealed black 96-well plate (Costar) at 37° C. Fluorescence polarization data were acquired periodically using a Perkin Elmer Victor³V plate reader. After nearly one week, the plate reader was equilibrated to 37° C., thrombin (12 U) was added to each well, and polarization was monitored at 12 min intervals. Solutions of the free fluorophores (100 nM) exhibited polarization values of 40±1.3 mP (AF488 $C_5$-aminooxyacetamide) and 104±0.3 mP (1c), consistent with those of the thrombin-cleaved products, with error attributable to the presence of a mixture of a peptide-AF488 conjugate and free fluorophore, as well as a slight increase in the concentration of AF488 conjugate solutions due to evaporation of PBS over the course of a week at 37° C.

F. Preparation and Evaluation of AF488-α-HER2

FGly-α-HER2 was prepared as previously described and Cys to FGly conversion was 97% complete (Cho H, et al. (2011), "Optimized clinical performance of growth hormone with an expanded genetic code," Proc. Natl. Acad. Sci. USA 108(22):9060-9065)).

Preparation of AF488-α-HER2: FGly-α-HER2 (76 μg) was incubated with 1c (1 mM) in sodium acetate buffer (100 mM, pH 4.50) in a 100 μL reaction volume at 37° C. for 12 h. The solution was then diluted 10-fold and exchanged into PBS 6 times using a centrifugal concentrator (Amicon Ultra, 30 kDa MWCO). The conjugation efficiency was determined on a Thermo NanoDrop 2000 spectrophotometer, using $E_{280}=210000$ $M^{-1}$ $cm^{-1}$ for FGly-α-HER2, $\epsilon_{494}=71000$ $M^{-1}$ $cm^{-1}$ for AF488, and applying a correction factor to account for absorption of AF488 at 280 nm ($\epsilon_{280}=\epsilon_{494}*0.11$).

Cell culture: SKOV3 and Jurkat T cells were obtained from ATCC and grown in a humidified 5% $CO_2$ atmosphere at 37° C. in RPMI-1640 media supplemented with glutamine, 10% fetal bovine serum, and penicillin/streptomycin. Cell density was kept between $1\times10^5$ and $2\times10^6$ cells/mL.

Live cell labeling with AF488-α-HER2: Cells in culture media were harvested and washed with FACS buffer (1% fetal bovine serum in PBS) and resuspended at $10^6$/mL in FACS buffer in 100 μL aliquots in a 96-well V-bottom plate (Costar), then cooled to 4° C. (all subsequent manipulations were performed at 4° C.). Labeling experiments were performed in triplicate. All antibody incubations were carried out in 100 μL FACS buffer, and all washing steps entailed centrifugation at 300×g and washing 3 times with 200 μL FACS buffer. Cells were incubated with hIgG (10 nM) for 30 min, washed, incubated with rabbit α-AF488 (Life Technologies, 1/2000) or vehicle for 30 min, washed, and then incubated with goat α-hIgG DyLight 649 (Jackson ImmunoResearch, 1/2000) and donkey α-rabbit FITC (Jackson ImmunoResearch, 1/2000) or vehicle for 30 min. The cells were then washed, resuspended in 300 μL FACS buffer, and analyzed by flow cytometry. Flow cytometry was performed on a BD FACSCalibur flow cytometer and data analysis was performed in FlowJo (Tree Star). Median fluorescence intensity was calculated on populations gated as shown in FIG. 13.

Results and Discussion

Design and synthesis of Pictet-Spengler ligation reagents. For the last century, the Pictet-Spengler reaction has played an important role in the synthesis of indole alkaloid natural products (Stöckigt J, Antonchick A P, Wu F, & Waldmann H (2011), "The Pictet-Spengler Reaction in Nature and in Organic Chemistry," *Angew. Chem. Int. Ed.* 50(37):8538-8564). We hypothesized that the transformation (FIG. 1A), which forms a C—C bond between tryptamine and an aldehyde or a ketone, could be adapted for the purpose of irreversible bioconjugation. The canonical Pictet-Spengler reaction has previously been used in this context (Sasaki T, Kodama K, Suzuki H, Fukuzawa S, & Tachibana K (2008), "N-terminal labeling of proteins by the Pictet-Spengler reaction," *Bioorg. Med. Chem. Lett.* 18(16):4550-4553); however, the reaction is slow under protein-compatible conditions, proceeding with a second-order rate constant of approximately $10^{-4}$ $M^{-1}$ $s^{-1}$ at pH 4-5 (Maresh J J, et al. (2007), "Strictosidine Synthase: Mechanism of a Pictet-Spengler Catalyzing Enzyme," *J. Am. Chem. Soc.* 130(2):710-723). These slow reaction kinetics necessitate high concentrations (e.g., 50 mM) of the derivatizing reagent to achieve good yields of modified protein, which can be problematic from the standpoints of reagent cost, off-target reactivity, purification of the resulting conjugate, and toxicity if applied to protein labeling on live cells.

In our design of the Pictet-Spengler ligation (FIG. 1B), we increased the rate of the reaction by moving the aminooxy substituent to the 2-position of the indole, allowing the more nucleophilic 3-position to engage in electrophilic substitution. Indoles that are substituted with aliphatic amines at the 2-position are known to engage in "iso-Pictet-Spengler" reactions in organic solvents (Molina P, Alca'ntara Jn, & Lo'pez-Leonardo C (1996), "Regiospecific preparation of γ-carbolines and pyrimido[3,4-a]indole derivatives by intramolecular ring-closure of heterocumulene-substituted indoles," *Tetrahedron* 52(16):5833-5844; Lee Y, Klausen R S, & Jacobsen E N (2011), "Thiourea-Catalyzed Enantioselective Iso-PictetSpengler Reactions," *Org. Lett.* 13(20):5564-5567). Finally, we methylated the aminooxy functionality to provide a reactive oxyiminium ion intermediate that would facilitate rapid C—C bond formation via intramolecular electrophilic substitution. Pictet-Spengler reactions of N-alkoxytryptamines to afford products with exocyclic aminooxy functionality are known (Plate R, Van Hout R H M, Behm H, & Ottenheijm H C J (1987), "Synthesis of 2-hydroxy-3-(ethoxycarbonyl)-1,2,3,4-tetrahydro-β-carbolines from N-hydroxytryptophans. An approach to the eudistomin series," *J. Org. Chem.* 52(4):555-560); Hermkens P H H, et al. (1990), "Syntheses of 1,3-disubstituted N-oxy-β-carbolines by the PictetSpengler reactions of N-oxy-tryptophan and -tryptamine derivatives," *Tetrahedron* 46(3):833-846); Kirkup M P, Shankar B B, McCombie S, Ganguly A K, & McPhail A T (1989), "A concise route to the oxathiazepine containing eudistomin skeleton and some carba-analogs," *Tetrahedron Lett.* 30(49):6809-6812), but to the best of our knowledge neither their kinetics nor their behavior in aqueous media has been studied. With these precedents, we expected aminooxy-functionalized indoles 1 to engage in a fast Pictet-Spengler type reaction (FIG. 1B).

We prepared model indole 1a in a short, high-yielding synthesis (FIG. 1C). First, an ester was installed as a masked functionalization handle by protection of indole-2-methanol with TBSCl followed by a DBU-catalyzed aza-Michael addition to methyl acrylate (Yeom C-E, Kim M J, 8: Kim B M (2007), "1,8-Diazabicylo[5.4.0]undec-7-ene (DBU)-promoted efficient and versatile aza-Mchael addition," *Tetrahedron* 63(4):904-909). Following deprotection of the hydroxyl group to yield indole 2, the aminooxy moiety was installed by reaction with Teoc-protected Nmethylhydroxylamine under modified Mitsunobu conditions (Ishikawa T, et al. (2001), Novel [2-3]-Sigmatropic Rearrangement for Carbon—Nitrogen Bond Formation *J. Am. Chem. Soc.* 123 (31):7734-7735; Tsunoda T, Yamamiya Y, & Itô S (1993), 1,1'-(azodicarbonyl)dipiperidine-tributylphosphine, a new reagent system for mitsunobu reaction, *Tetrahedron Lett.* 34(10):1639-1642). Saponification of the resulting product yielded compound 3, which was cleanly deprotected with CsF to afford indole 1a in 66% yield over 6 steps.

Figures 6A, 6B:
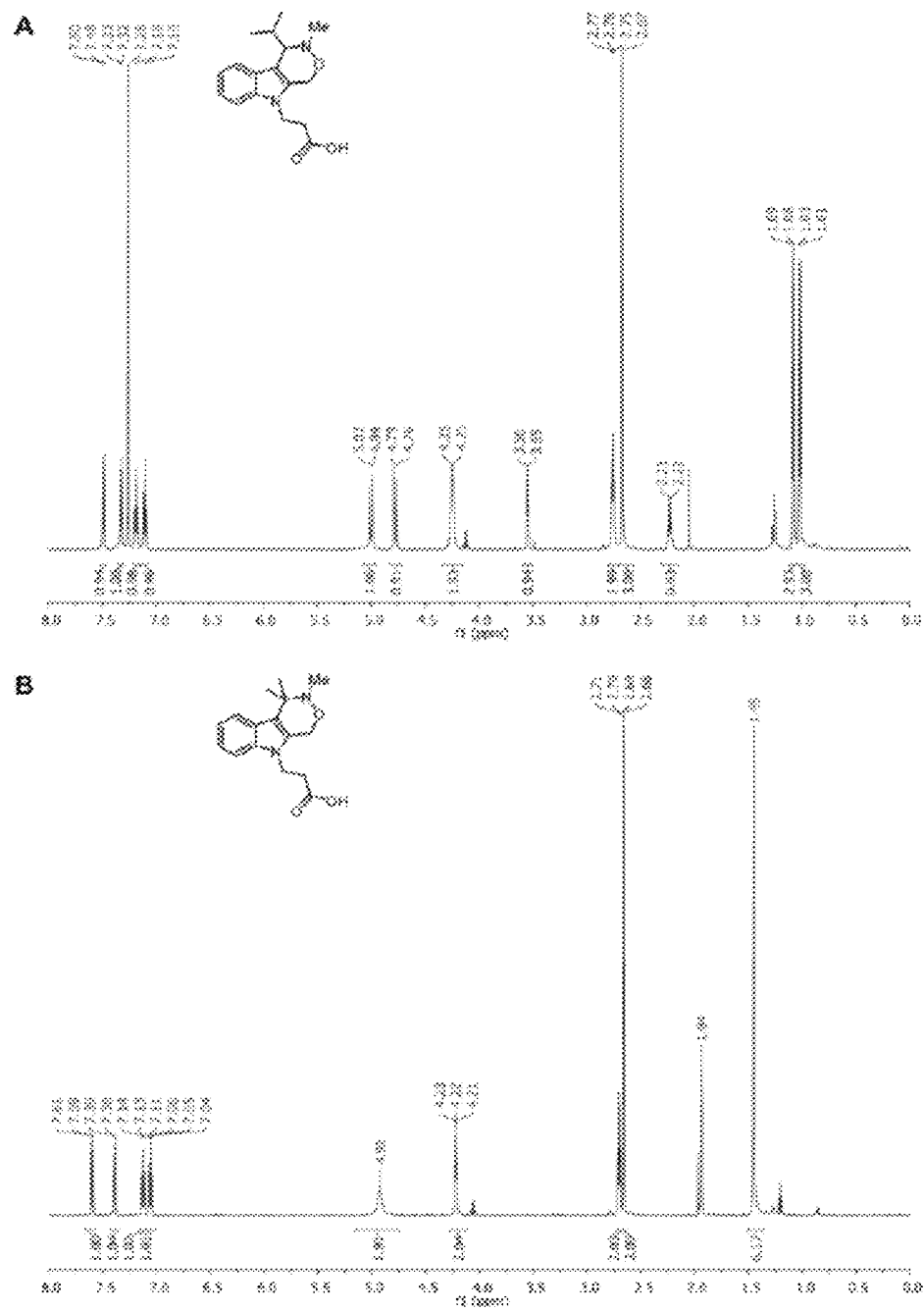
FIG. 6A-FIG. 6B $^1$HNMR spectra of crude material from reaction of 1a with (A) isobutyraldehyde and (B) acetone.

Reactivity of model indole 1a and hydrolytic stability of products. To validate the Pictet-Spengler ligation, we treated indole 1a with either isobutyraldehyde or acetone in methanolic ammonium acetate solutions at pH 4.5. Both reactions proceeded very cleanly in less than 1 hour to afford the desired trihydro-β-oxa-γ-carboline (hereafter referred to as oxacarboline) products (FIG. 6). Analysis of the rate of the reaction of 1a with isobutyraldehyde in $D_2O$ by $^1H$ NMR spectroscopy revealed a rate law that is first-order in the concentrations of 1a and isobutyraldehyde at pD 7.0 (Table S1), and a pD-rate constant profile characteristic of aminooxy compounds under acidic conditions (FIG. 1D) (Jencks WP (1959) Studies on the Mechanism of Oxime and Semicarbazone Formation *J. Am. Chem. Soc.* 81(2):475-481). These results show that our rate-enhancement strategies were successful, as the Pictet-Spengler ligation is 4-5 orders of magnitude faster than the canonical Pictet-Spengler reaction in aqueous media.

Figure 2A:
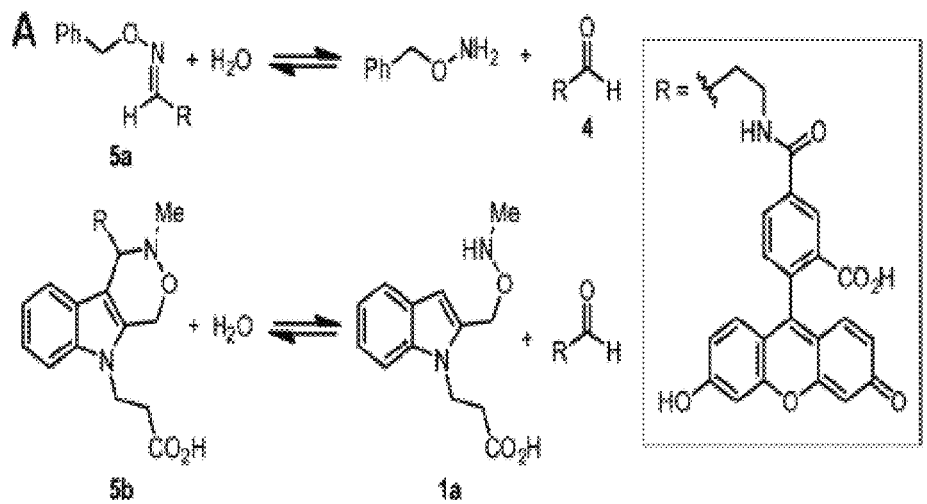
-FIG. 2B shows hydrolytic stability of a model oxime and oxacarboline. (A) Scheme showing hydrolysis of 5a and 5b. (B) Liquid chromatography data showing hydrolysis of 1 μM 5a and 5b at room temperature over two days.
Figure 2B:
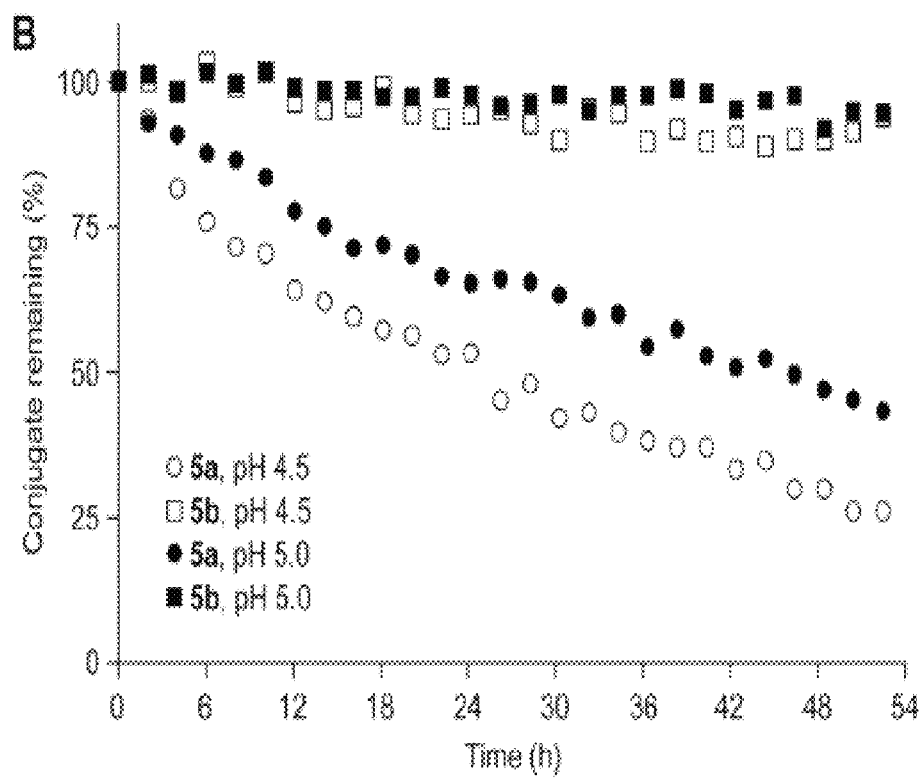
Figure 7:
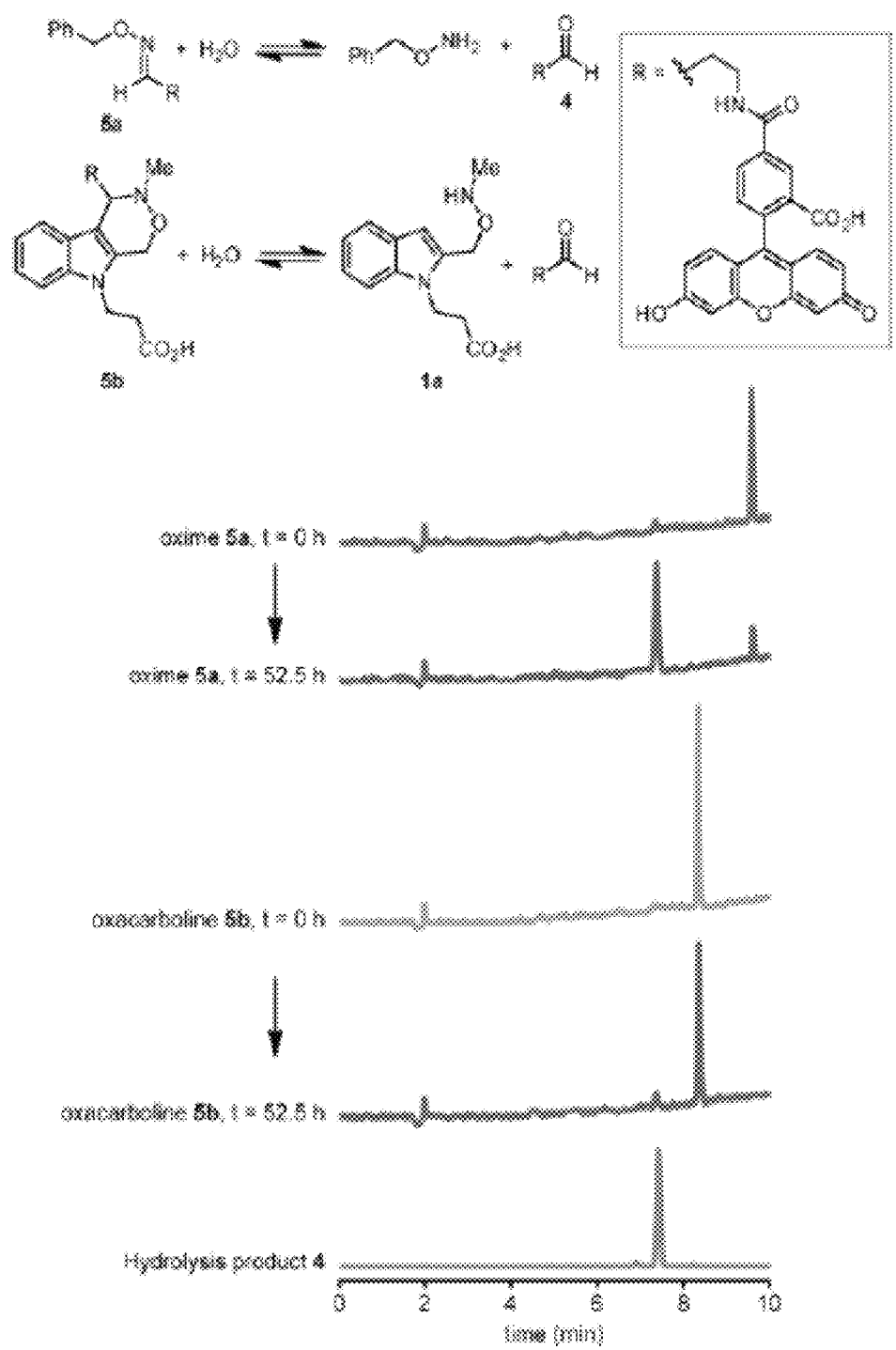
FIG. 7 Liquid chromatographs (A$_{440}$) showing hydrolysis of 1 μM 5a and 5b in 5 μM sodium acetate pH 4.50 at room temperature. Compound 4 was synthesized independently and the intensity of its chromatograph is arbitrarily scaled. Samples were analyzed using a gradient of 5 to 95% acetonitrile in $H_2O$ with 0.1% trifluoroacetic acid.
Figure 8A:
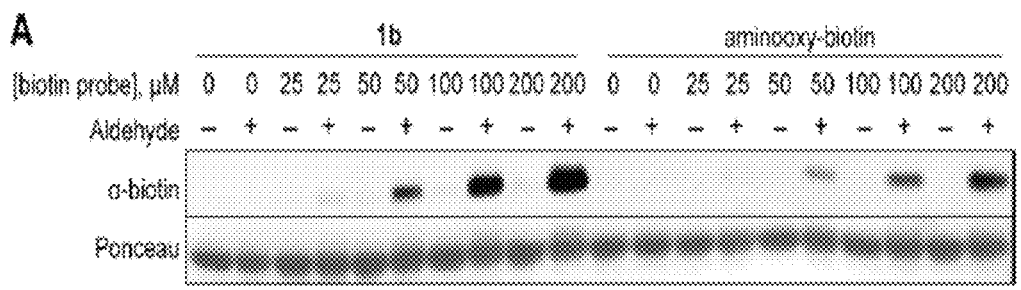
FIG. 8A-FIG. 8E Biotinylation of glyoxal-Mb via oxacarboline or oxime formation under a variety of conditions. Mb or glyaxal-Mb was treated with 1b or commercially available N-(aminooxyacetyl)-$N^1$-(D-biotinoyl)hydrazine. Conditions: (A) 0-200 µM biotin probe for 3 h. at pH 4.0, (B) 250 µM biotin probe for 0-2 h at pH 4.0, (C) 250 µM biotin probe for 3 h at pH 4.0-7.5, (D) 100 µM biotin probe for 3 h at pH 4.5 in the presence of 0-800 µM $BnONH_2$, or (E) 100 µM 1b for 4 h at pH 4.5, 5.5, or 6.5 in the presence of 0-50 µM buffered aniline. All reactions were run at 37° C. and quenched with 10 µM benzaldehyde prior to resolution by SDS-PAGE. Biotinylation was assessed with a FITC-conjugated α-biotin antibody and total protein loading with Ponceau S.
Figure 8B:
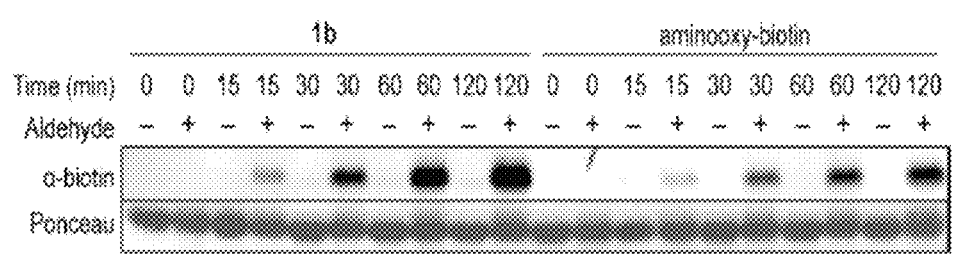
Figure 8C:
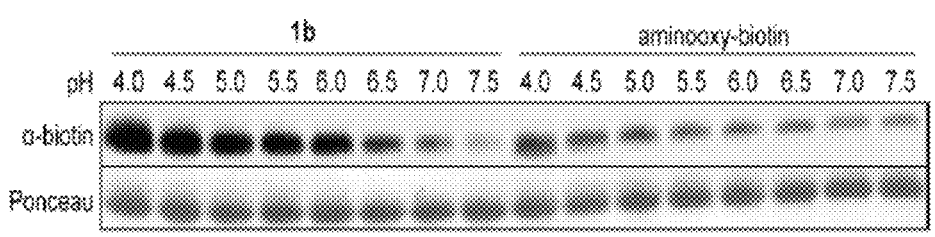
Figure 8D:
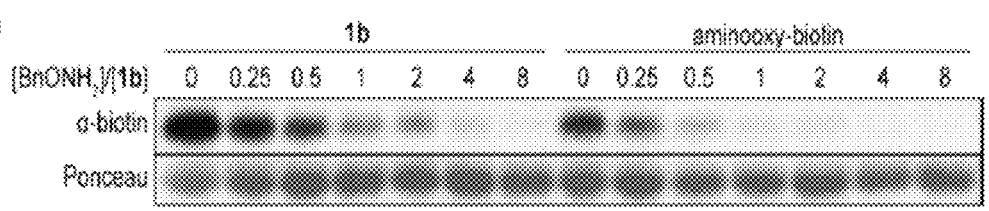
Figure 8E:
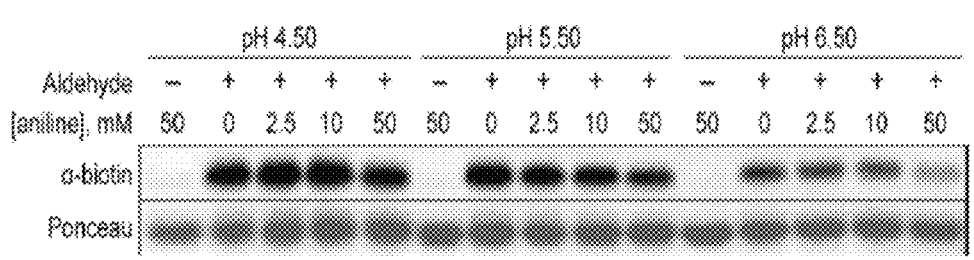

Next, we compared the hydrolytic stability of the oxacarboline generated by the Pictet-Spengler ligation with that of a model oxime. We treated an aldehyde-derivatized fluorescein (4, FIG. 2A) with benzylalkoxyamine or 1a to generate conjugates 5a and 5b, respectively. Buffered solutions at pH 4.5 or 5.0 containing 1 µM 5a or 5b were incubated at room temperature and analyzed by liquid chromatography. Over the course of two days, the majority of oxime 5a hydrolyzed while over 90% of oxacarboline 5b remained intact (FIG. 2B); no other products were detected (FIG. 7). Previous work has shown that oxime hydrolysis occurs on a similar timescale in the presence of excess formaldehyde used as a trap to drive the reaction toward hydrolysis of the conjugate (Kalia J & Raines R T (2008), "Hydrolytic Stability of Hydrazones and Oximes," *Angew. Chem. Int. Ed.* 47(39):7523-7526). Notably, our results indicate that oxime hydrolysis can occur to an appreciable extent in aqueous solution, even in the absence of a trap, underscoring the need for irreversible bioconjugation reactions. These model experiments establish that the Pictet-Spengler ligation proceeds rapidly under acidic conditions to yield a hydrolytically stable product.

Figures 3A, 3B, 3C, 3D, 3E:
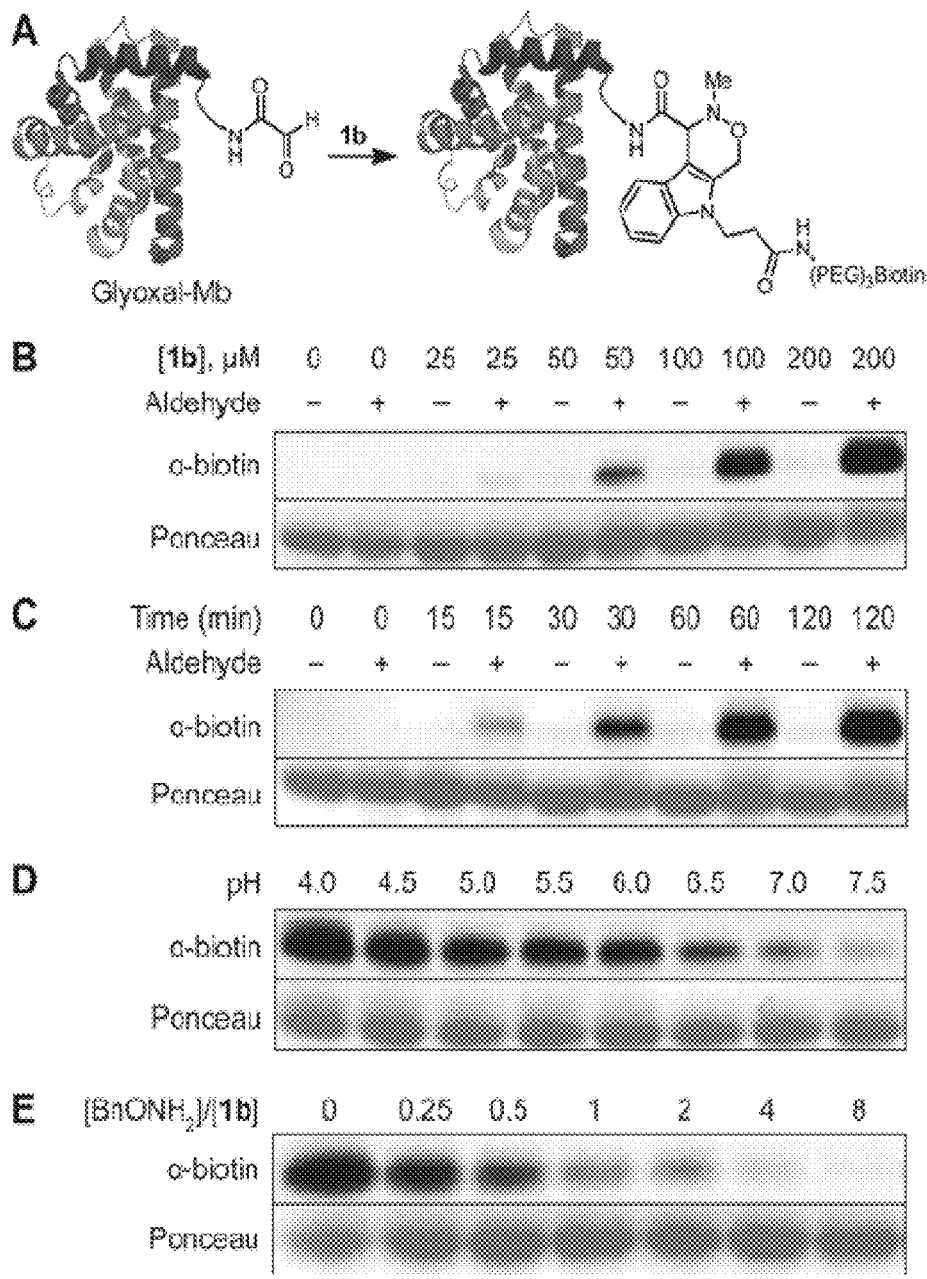
FIG. 3A-FIG. 3E. Optimization of the Pictet-Spengler ligation on glyoxal-Mb. (A) General scheme for biotinylation of glyoxal-Mb. Indole 1b exhibits (B) concentration-dependent (C) time-dependent and (D) pH-dependent labeling of glyoxal-Mb. Additionally, (E) biotinylation can be diminished by co-treatment with BnONH$_2$. Mb (-aldehyde) or glyoxal-Mb (+aldehyde) were treated with (B) 0-200 μM 1b for 3 h at pH 4.0, (C) 250 μM 1b for 0-2 h at pH 4.0, (D) 250 μM 1b for 3 h at pH 4.0-7.5, or (E) 100 μM 1b for 3 h at pH 45 in the presence of 0-800 μM BnONH$_2$. All reactions were run at 37° C. and quenched with 10 μM benzaldehyde prior to resolution by SDS-PAGE. Biotinylation was assessed with a fluorescein isothiocyanate (FITC)-conjugated α-biotin antibody and total protein loading with Ponceau S.

Scope of the reaction on model proteins. We next evaluated the Pictet-Spengler ligation as a means to label aldehyde-bearing proteins. To facilitate the detection and manipulation of labeled proteins, we prepared biotinylated indole 1b by coupling 3 with amino-poly(ethylene glycol)-functionalized biotin, followed by deprotection of the Teoc group with CsF. As a protein substrate for reaction with 1b, we generated horse heart myoglobin with an N-terminal glyoxal moiety (glyoxal-Mb) by pyridoxal phosphate-mediated transamination (FIG. 3A) (Gilmore J M, Scheck R A, Esser-Kahn A P, Joshi N S, & Francis M B (2006), "N-Terminal Protein Modification through a Biomimetic Transamination Reaction," *Angew. Chem. Int. Ed.* 45(32):5307-5311). In glyoxal-Mb labeling experiments, conjugated product was detected by SDS-PAGE and Western blotting with a FITC-conjugated α-biotin antibody after quenching excess labeling reagent with benzaldehyde. First, we established that labeling occurs in a concentration- and time-dependent manner (FIGS. 3B and 3C, respectively). Importantly, control samples of Mb that were not aldehyde-functionalized showed negligible labeling. We next studied the pH dependence of the reaction, observing a greater extent of biotinylation at more acidic pH (FIG. 3D) as also observed in kinetic studies of indole 1a. Finally, we found that co-treatment with benzylalkoxyamine as an aldehyde scavenger resulted in diminished biotinylation (FIG. 3E). A similar series of experiments using commercial aminooxy-biotin as a labeling reagent showed the same qualitative trends in labeling (FIG. 8). Collectively, these results establish that indole 1b specifically labels the aldehyde functionality in transaminated myoglobin, and, more generally, behaves like a typical aminooxy reagent (We also explored whether the Pictet-Spengler ligation could be accelerated by aniline catalysis (see Dirksen A, Hackeng T M, & Dawson P E (2006), "Nucleophilic Catalysis of Oxime Ligation," *Angew. Chem. Int. Ed.* 45(45):7581-7584). Aniline did not increase the rate of the reaction of Ib with glyoxal-Mb at pH 4.5, and at higher pH (5.5 or 6.5) aniline was found to inhibit the reaction (FIG. 8E), consistent with previous observations (Hudak J E, et al. (2012), "Synthesis of Heterobifunctional Protein Fusions Using Copper-Free Click Chemistry and the Aldehyde Tag," *Angew. Chem. Int. Ed.* 51(17):4161-4165; Shi X. et al. (2012), "Quantitative fluorescence labeling of aldehyde-tagged proteins for single molecule imaging," *Nat. Methods* 9(5):499-503)).

Figures 4A, 4B, 4C, 4D:
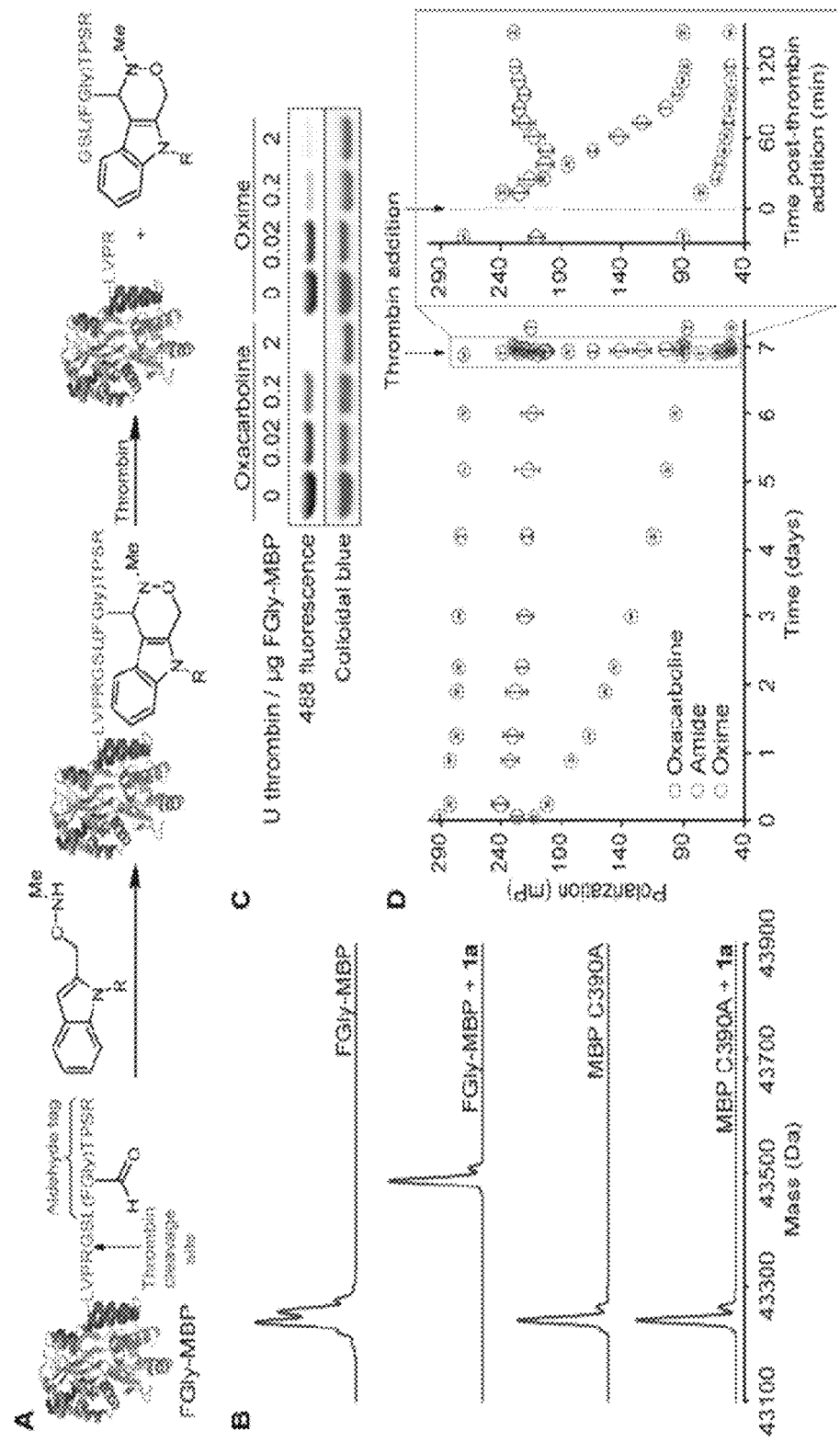
FIG. 4A-FIG. 4D. Modification of FGly-MBP by the Pictet-Spengler ligation. (A) Scheme depicting Pictet-Spengler ligation with FGly-MBP followed by thrombin-catalyzed cleavage of a C-terminal 8 mer peptide containing the oxacarboline. (B) ESI-MS analysis of Pictet-Spengler ligations. FGly-MBP and MBP C390A were incubated with 1 mM 1a at pH 5.0 for 12 h at 37° C. (C) Thrombin-catalyzed cleavage of FGly-MBP conjugates. Fluorescence of AF488-MBP conjugates decreased at higher [thrombin], consistent with labeling exclusively at the C-terminus (D) Fluorescence polarization analysis of AF488-MBP conjugate hydrolysis; inset shows polarization of solutions immediately following thrombin addition. Solutions containing 100 nM AF488 conjugate were incubated in phosphate-buffered saline (pH 7.2) at 37° C. for one week prior to thrombin addition.
Figures 9A, 9B:
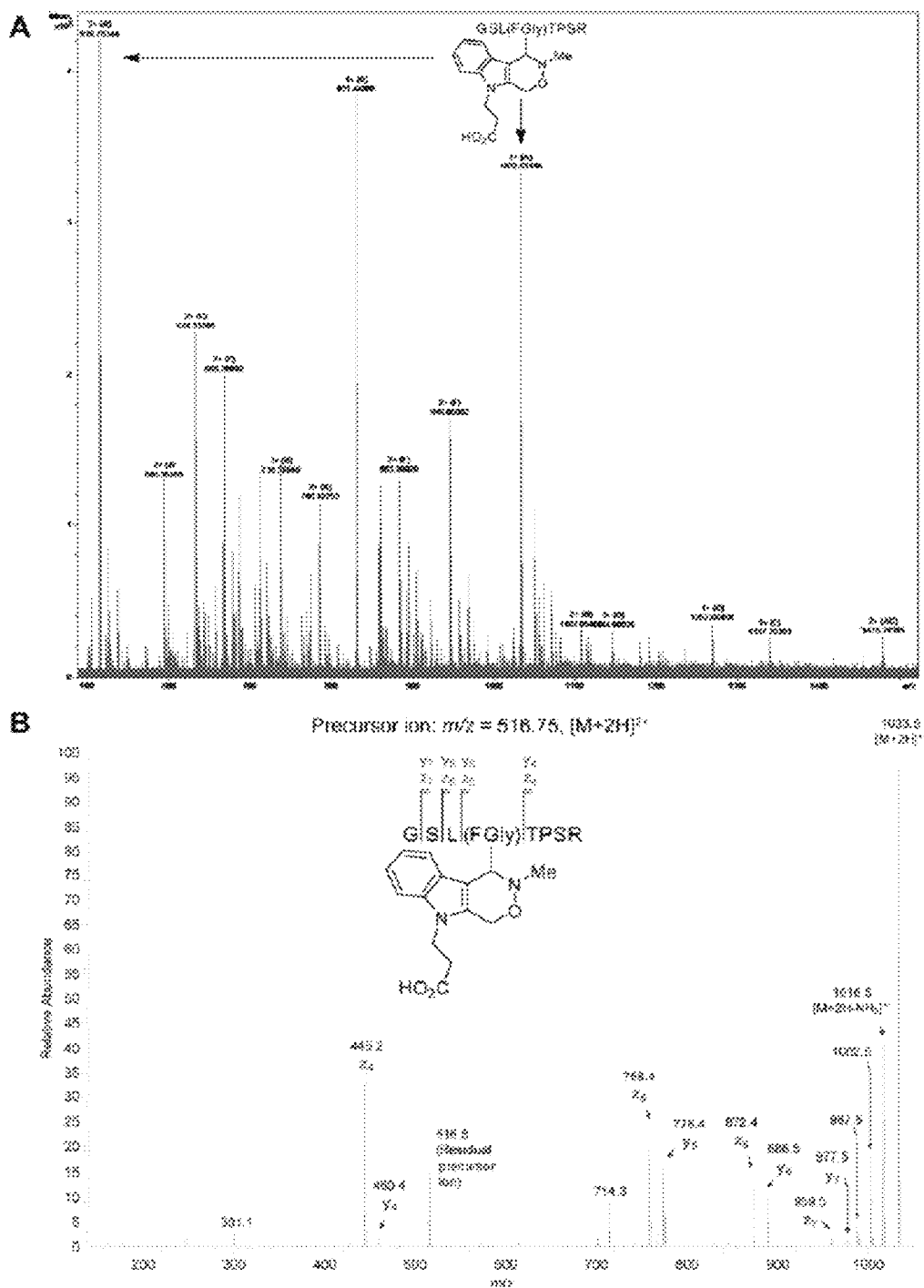
FIG. 9A-FIG. 9B Mass spectrometric analysis of cryptic digests of FGly-MBP conjugated to 1a. (A) High-resolution ESI-MS spectrum showing modified peptide. Calculated mass: 1032.5114; observed: 1032,5220. (B) MS/MS fragmentation of modified peptide by electron-transfer dissociation.

We next studied the reaction of 1a with formylglycine-functionalized maltose-binding protein (FGly-MBP), prepared using the genetically-encoded aldehyde tag method (FIG. 4A) (Rabuka D, Rush J S, deHart G W, Wu P, & Bertozzi C R (2012), "Site-specific chemical protein conjugation using genetically encoded aldehyde tags," *Nat. Protoc.* 7(6):1052-1067). Briefly, the 6-residue peptide sequence LCTPSR was engineered at the C-terminus of MBP, constituting residues 389-394 in the recombinant protein. We also included a thrombin cleavage site N-terminal to the aldehyde tag sequence. Coexpression of the protein alongside the *M. tuberculosis* FGE in *E. coli* resulted in oxidation of Cys390 to FGly (Carrico I S, Carlson B L, & Bertozzi C R (2007), "Introducing genetically encoded aldehydes into proteins," *Nat. Chem. Biol.* 3(6):321-322). As a control, we also expressed the C390A mutant, which is not a substrate for FGE and lacks the FGly aldehyde. Incubation of FGly-MBP with 1 mM indole 1a at 37° C. for 12 hours resulted in quantitative conversion to the desired singly-modified adduct, as judged by ESI-MS, whereas the C390A mutant showed no reaction (FIG. 4B). Additionally, when an FGly-MBP conjugate of 1a was digested with trypsin, we were able to identify the C-terminal 8-residue tryptic peptide containing the desired adduct by high-resolution ESI-MS. MS/MS fragmentation of the tryptic peptide by electron-transfer dissociation provided direct evidence for modification of the FGly residue (FIG. 9B).

To confirm that labeling occurred only at the FGly residue, we exploited the thrombin cleavage site engineered directly upstream of the aldehyde tag sequence. First, we prepared indole 1c by coupling 3 with Alexa Fluor 488 (AF488) cadaverine followed by deprotection with CsF. Next, we prepared oxacarboline- or oxime-linked AF488 conjugates of FGly-MBP by treatment with either 1c or AF488 hydroxylamine, incubated the conjugates with various amounts of thrombin for 1 hour, and then analyzed the products by SDS-PAGE. The intensity of in-gel fluorescence from the FGly-MBP band decreased at higher thrombin concentrations, consistent with labeling exclusively within the cleaved C-terminal 8-residue peptide (FIG. 4C). Notably, the oxime- and oxacarboline-linked AF488-MBP conjugates displayed qualitatively similar behavior, indicating that, relative to the oxime, the larger oxacarboline moiety did not inhibit the protein's ability to serve as a substrate for thrombin. These experiments establish that the Pictet-Spengler ligation exclusively labels the FGly residue on the aldehyde tagged protein.

Figure 10:
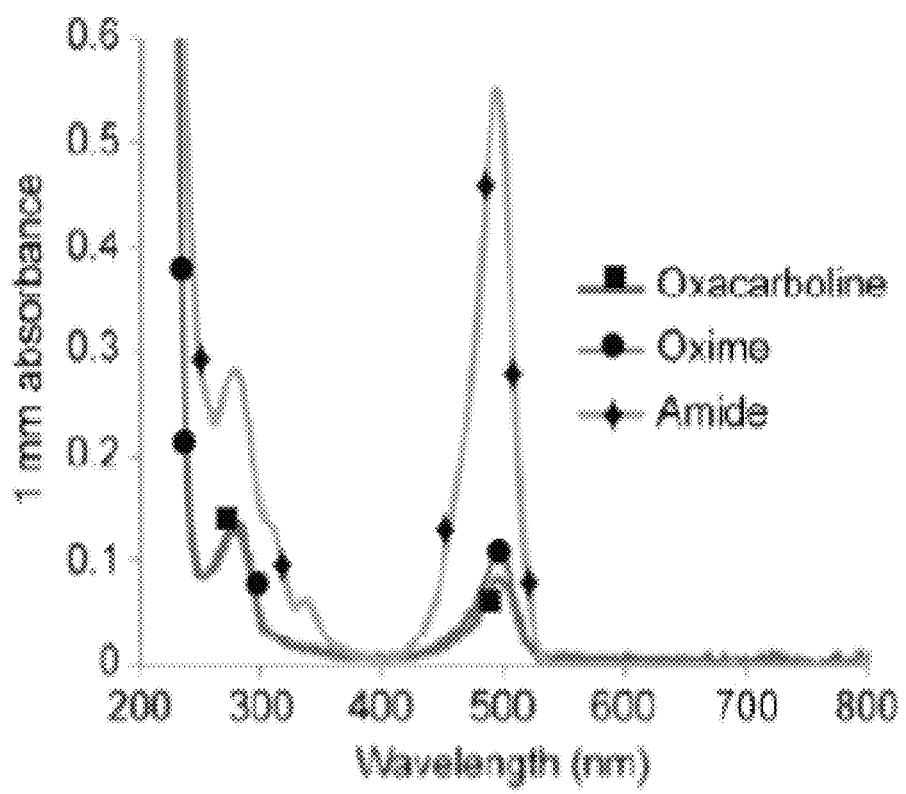
FIG. 10 UV-vis spectrum of AF488-MBP conjugates in PBS.

Hydrolytic stability of the oxacarboline linkage on a protein. Next, we assayed the hydrolytic stability of the oxacarboline linkage on FGly-MBP. Fluorescence polarization is a technique that yields information about the tumbling rate of a fluorophore in solution: macromolecule-conjugated fluorophores tumble slowly and exhibit high polarization values, whereas small molecule fluorophores exhibit low polarization values. Thus, fluorescence polarization is ideally suited to monitor cleavage of proteinfluorophore conjugates (Jameson D M & Ross J A (2010), "Fluorescence Polarization/Anisotropy in Diagnostics and Imaging," *Chem. Rev.* 110(5):2685-2708). A solution of FGly-MBP was treated with 1c, AF488 hydroxylamine, or a lysine-reactive AF488-sulfodichlorophenol ester to make oxacarboline-, oxime-, or amide-linked AF488-MBP conjugates (FIG. 10). The samples were then diluted to 100 nM in AF488 conjugate and incubated at 37° C. The fluorescence polarization was monitored for one week (FIG. 4D). The oxime conjugate exhibited a steady drop in polarization, indicating nearly complete hydrolysis of the conjugate over the course of 7 days. In contrast, the oxacarboline and amide conjugates showed only a minimal change in polarization. To confirm that the oxacarboline-linked AF488 conjugate was still intact after one week, we added thrombin to the samples, which resulted in an immediate decrease in polarization as the C-terminal peptide containing the fluorophore was cleaved from the rest of the protein. The signal from the amidelinked AF488 conjugate remained stable (no lysine residues are present downstream of the thrombin cleavage site), indicating that the decrease in polarization was not an artifact of thrombin addition.

Figures 5A, 5B:
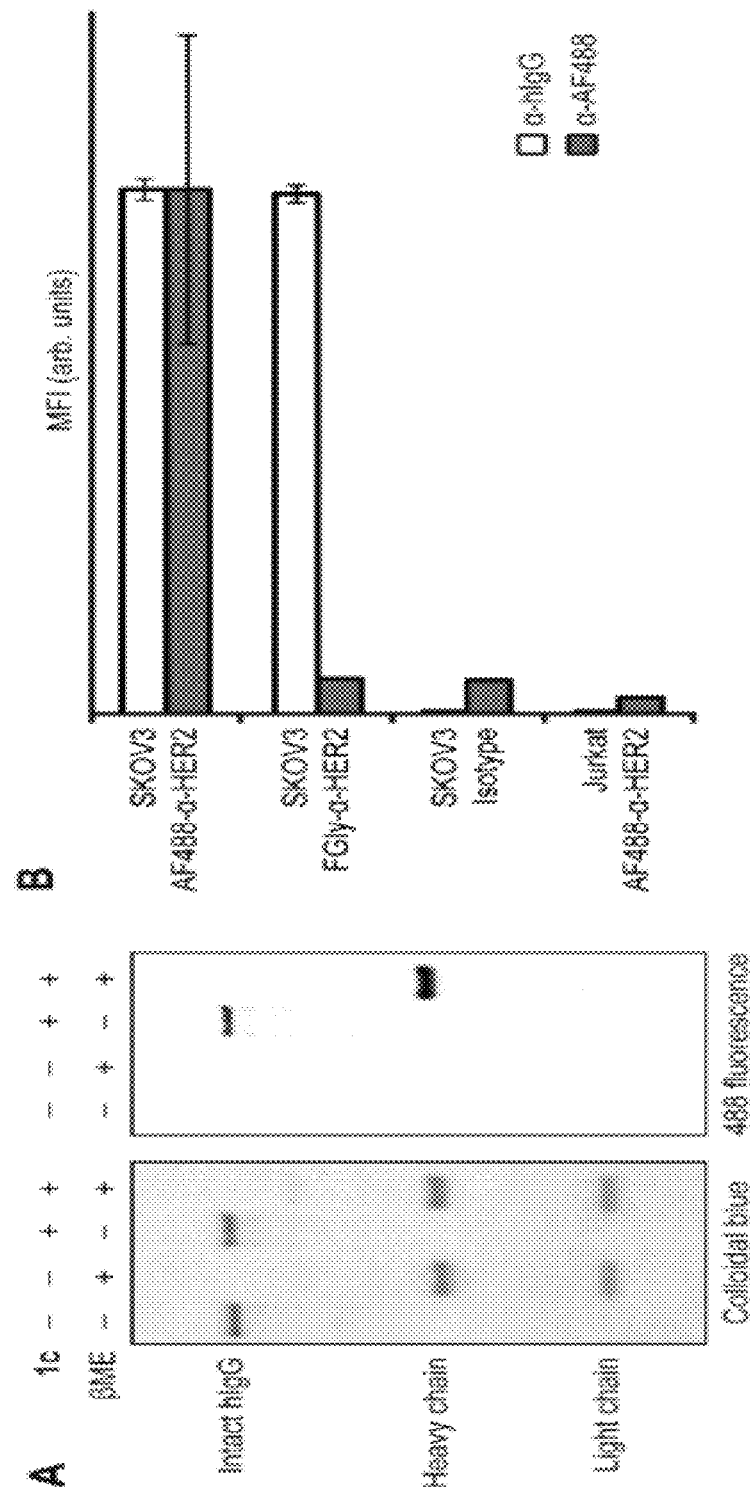
FIG. 5A-FIG. 5B. Characterization of FGly-α-HER2 modified by the Pictet-Spengler ligation. (A) Reducing and non-reducing SDS-PAGE analysis of FGly-α-HER2 and AF488-α-HER2. (B) Median fluorescence intensity of SKOV3 and Jurkat cell populations treated with human antibodies. Cells were treated with AF488-α-HER2, FGly-α-HER2 or human isotype control and then fluorescently labeled with α-hIgG and α-AF488 antibodies. Error bars represent standard deviation of three replicate experiments.
Figure 11:
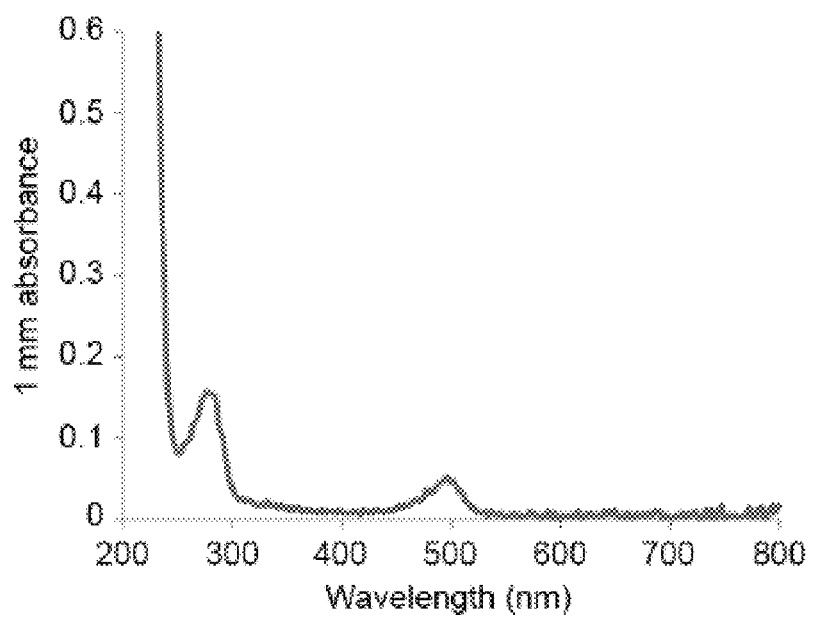
FIG. 11 UV-vis spectrum of AF488-α-HER2 conjugate in PBS.
Figures 12A, 12B:
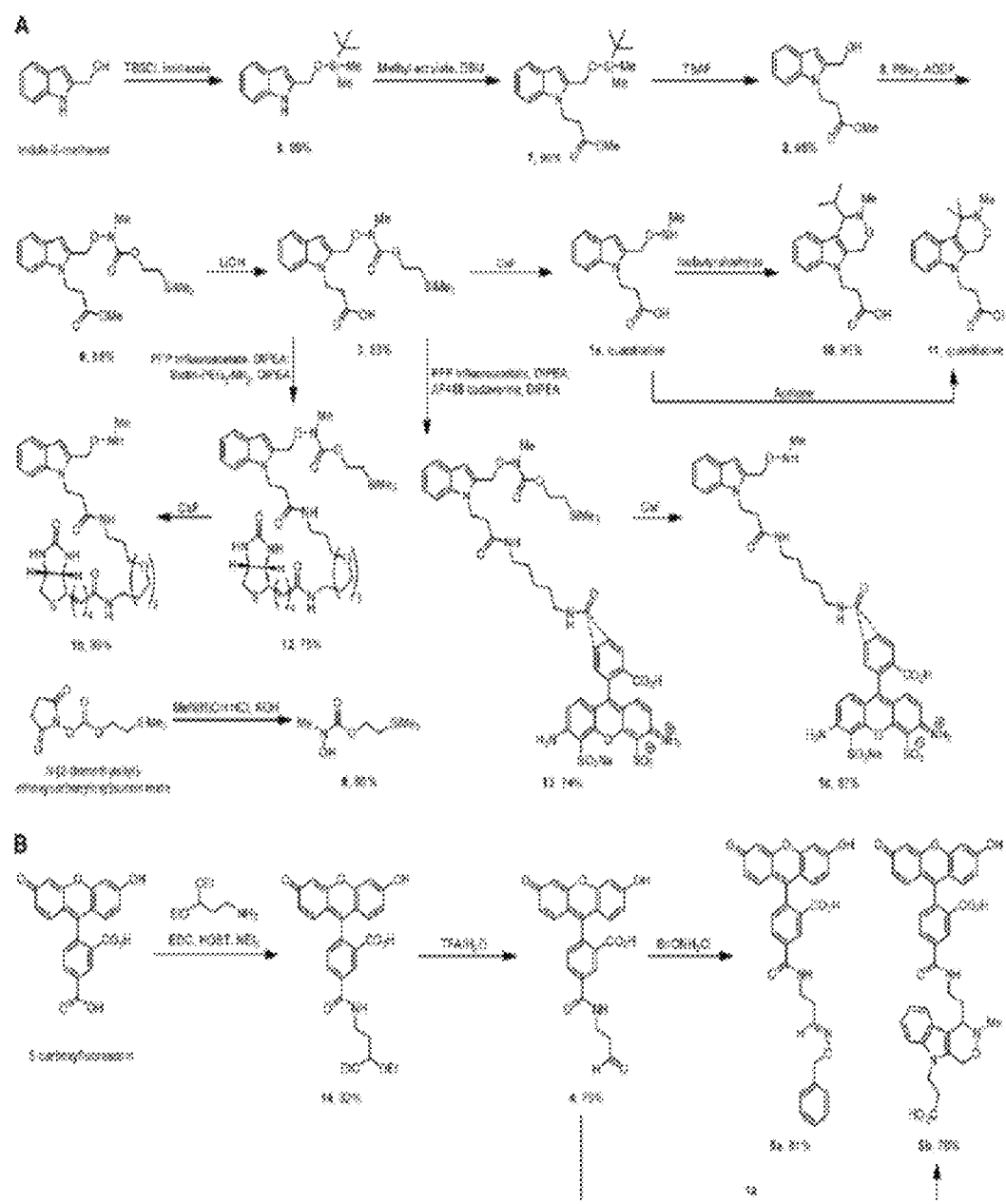
FIG. 12A-FIG. 12B Complete synthetic scheme showing preparation of (A) indoles and compounds required for their preparation, and (B) fluorescein derivatives used in small molecule hydrolysis experiments.

Application of the Pictet-Spengler ligation to site-specific modification of a monoclonal antibody. To showcase the utility of the Pictet-Spengler ligation in preparation of antibody conjugates, we used an α-HER2 human IgG modified with an aldehyde tag sequence at the C-terminus of each of its two heavy chains (abbreviated FGly-α-HER2). The parent antibody is a variant of the clinically approved drug Herceptin (Menard S, Pupa S M, Campiglio M, & Tagliabue E (2003), "Biologic and therapeutic role of HER2 in cancer," *Oncogene* 22(42):6570-6578) and of T-DM1, an antibody-drug conjugate based on Herceptin that is presently in latestage clinical evaluation (Krop I E, et al. (2012), "A Phase II Study of Trastuzumab Emtansine in Patients With Human Epidermal Growth Factor Receptor 2-Positive Metastatic Breast Cancer Who Were Previously Treated With Trastuzumab, Lapatinib, an Anthracycline, a Taxane, and Capecitabine," *Journal of Clinical Oncology*). FGly-α-HER2 was prepared as previously described (Hudak J E, et al. (2012), "Synthesis of Heterobifunctional Protein Fusions Using Copper-Free Click Chemistry and the Aldehyde Tag," *Angew. Chem. Int. Ed.* 51(17):4161-4165) and then labeled with indole 1c at pH 4.5 for 12 h; the resulting conjugate (AF488-α-HER2) was cleanly modified on the heavy chain (FIG. 5A) with an average of 1.0±0.13 fluorophores per hIgG (FIG. 11). We next assessed binding of this antibody conjugate to the ovarian adenocarcinoma cell line SKOV3, which overexpresses HER2, by flow cytometry. SKOV3 cells were treated with AF488-α-HER2 or FGly-α-HER2, followed by a DyLight 649-conjugated α-hIgG secondary antibody to measure total hIgG binding. We found no difference in binding between AF488-α-HER2 and FGly-α-HER2 (FIG. 5B), suggesting that neither the Pictet-Spengler ligation reaction conditions nor the presence of the oxacarboline moiety negatively impacts the antibody's affinity for HER2. Incubation of the labeled cells with a rabbit α-AF488 secondary antibody followed by a FITC-conjugated α-rabbit tertiary antibody resulted in increased fluorescence on cells treated with AF488-α-HER2 but not with FGly-α-HER2 (FIG. 5B). This result confirms that the AF488 cargo was successfully delivered to the cell surface by AF488-α-HER2. As expected, an isotype control hIgG showed no significant binding to SKOV3 cells; furthermore, the AF488-α-HER2 conjugate had no affinity for Jurkat T cells, which do not express HER2. Overall, these experiments show that the Pictet-Spengler ligation can be used to prepare a site-specifically labeled monoclonal antibody without compromising binding activity.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

All publications, patents, and patent applications cited herein are hereby incorporated by reference in their entirety for all purposes.

What is claimed is:
1. A compound having the formula:

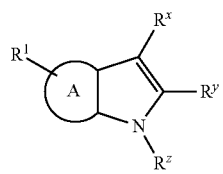

(I)

wherein
A is present or absent and, when present, is a substituted or unsubstituted aryl or heteroaryl moiety and $R^1$ is a member selected from H, substituted or unsubstituted alkyl, substituted or unsubstituted heteroalkyl, substituted or unsubstituted aryl, substituted or unsubstituted heteroaryl, halogen, CN, $CF_3$, acyl, $-SO_2NR^5R^6$, $-NR^5R^6$, $-OR^5$, $-S(O)_2R^5$, $-C(O)R^5$, $-COOR^5$, $-CONR^5R^6$, $-S(O)_2OR^5$, $-OC(O)R^5$, $-C(O)NR^5R^6$, $-NR^5C(O)R^6$, $-NR^5SO_2R^6$ and $-NO_2$ wherein $R^5$ and $R^6$ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl;

$R^x$, $R^y$ and $R^z$ are selected from H and substituted or unsubstituted alkyl and substituted or unsubstituted heteroalkyl with the proviso that at least one of $R^x$ and $R^y$ has a formula selected from:

(IIa)

wherein
$R^o$ is unsubstituted alkyl;
wherein
a member selected from $R^1$, $R^x$, $R^y$ and $R^z$ has the formula:

(III)

wherein
L is a linker selected from substituted or unsubstituted alkyl and substituted or unsubstituted heteroalkyl; and
X is selected from a detectable label, a crosslinking moiety, poly(ethylene glycol) and an affinity label.

2. The compound according to claim 1, having the formula:

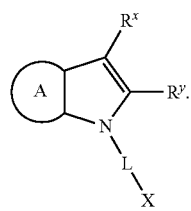

3. The compound according to claim 1, having a formula selected from:

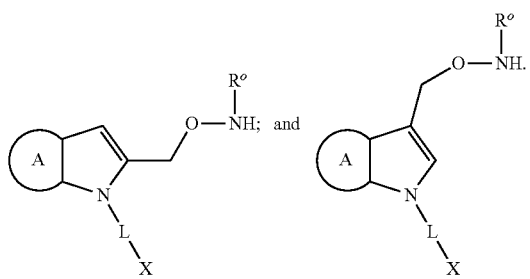

4. The compound according to claim 1, wherein said compound has the formula:

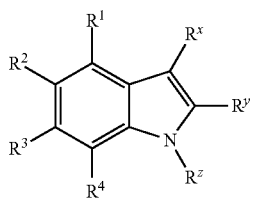

wherein
R¹, R², R³, and R⁴ are selected from H, substituted or unsubstituted alkyl, substituted or unsubstituted heteroalkyl, substituted or unsubstituted aryl, substituted or unsubstituted heteroaryl, halogen, CN, CF₃, acyl, —SO₂NR⁵R⁶, —NR⁵R⁶, —OR⁵, —S(O)₂R⁵, —C(O)R⁵, —COOR⁵, —CONR⁵R⁶, —S(O)₂OR⁵, —OC(O)R⁵, —C(O)NR⁵R⁶, —NR⁵C(O)R⁶, —NR⁵SO₂R⁶ and —NO₂, wherein two or more of R¹, R², R³, and R⁴, together with the atoms to which they are bonded, are optionally joined to form a ring system which is a member selected from substituted or unsubstituted cycloalkyl, substituted or unsubstituted heterocycloalkyl, substituted or unsubstituted aryl and substituted or unsubstituted heteroaryl; and R⁵ and R⁶ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

5. The compound according to claim 1, wherein L is substituted or unsubstituted alkyl having 1, 2, 3, 4, 5, 6, 7, 8, 9 or 10 carbon atoms.

6. The compound according to claim 1 wherein X is a member selected from a fluorophore and biotin.

7. The compound according to claim 1, wherein LX has the formula:

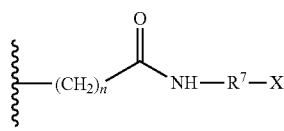

wherein
R⁷ is selected from substituted or unsubstituted alkyl and substituted or unsubstituted heteroalkyl; and
n is selected from 0, 1, 2, 3, 4, 5, 6, 7, 8, 9 and 10.

8. The compound according to claim 7, wherein R⁷ comprises:

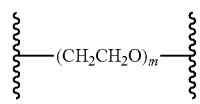

wherein
m is a selected from 1, 2, 3, 4, 5, 6, 7, 8, 9 or 10.

9. A method of modifying a biomolecule functionalized with a member selected from an aldehyde and a ketone, said method comprising:

(a) contacting said biomolecule with a compound according to claim 1 under reaction conditions appropriate to form a cyclized Pictet-Spengler adduct by reaction of said compound with a moiety selected from said aldehyde and said ketone, thereby modifying said biomolecule.

10. The method according to claim 9, wherein said adduct has a formula selected from:

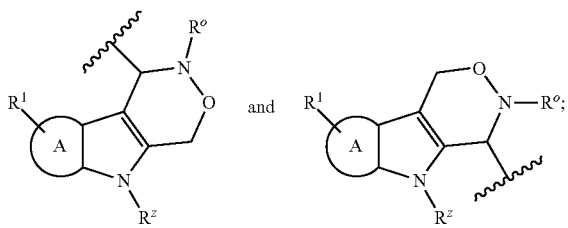

wherein
R¹ is selected from H, substituted or unsubstituted alkyl, substituted or unsubstituted heteroalkyl, substituted or unsubstituted aryl, substituted or unsubstituted heteroaryl, halogen, CN, CF₃, acyl, —SO₂NR⁵R⁶, —NR⁵R⁶, —OR⁵, —S(O)₂R⁵, —C(O)R⁵, —COOR⁵, —CONR⁵R⁶, —S(O)₂OR⁵, —OC(O)R⁵, —C(O)NR⁵R⁶, —NR⁵C(O)R⁶, —NR⁵SO₂R⁶ and —NO₂, wherein
R⁵ and R⁶ are members independently selected from H, substituted or unsubstituted alkyl, substituted or unsubstituted heteroalkyl, substituted or unsubstituted aryl, substituted or unsubstituted heteroaryl and substituted or unsubstituted heterocycloalkyl.

11. The method according to claim 9, wherein said adduct has a formula selected from:

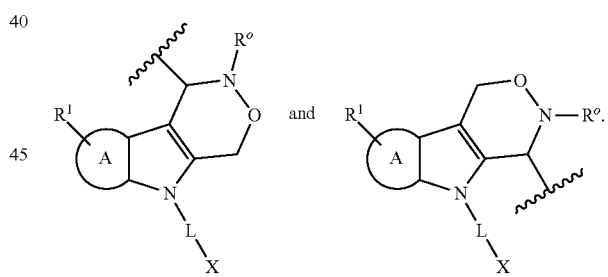

12. The method according to claim 9, wherein, prior to step (a), a precursor biomolecule is modified with a reactive moiety comprising a member selected from said aldehyde and said ketone, thereby forming said biomolecule functionalized with a member selected from an aldehyde and a ketone.

13. The method of claim 9 wherein said biomolecule is a member selected from a protein, a glycan, a nucleic acid, a metabolite, an inhibitor, a lipid, and a cofactor.

14. The method of claim 9, wherein said biomolecule is an antibody.

* * * * *

UNITED STATES PATENT AND TRADEMARK OFFICE
CERTIFICATE OF CORRECTION

PATENT NO. : 9,605,078 B2  
APPLICATION NO. : 14/443149  
DATED : March 28, 2017  
INVENTOR(S) : Carolyn Bertozzi et al.

Page 1 of 1

It is certified that error appears in the above-identified patent and that said Letters Patent is hereby corrected as shown below:

In the Specification

In Column 1, please amend the paragraph below the STATEMENT AS TO RIGHTS TO INVENTIONS MADE UNDER FEDERALLY SPONSORED RESEARCH AND DEVELOPMENT as follows:
This invention was made with Government support under Grant No. GM059907 awarded by the National Institutes of Health. The Government has certain rights in the invention.

Signed and Sealed this  
Eighth Day of May, 2018

Andrei Iancu  
*Director of the United States Patent and Trademark Office*